United States Patent [19]

Davies et al.

[11] Patent Number: 5,399,586

[45] Date of Patent: Mar. 21, 1995

[54] TREATMENT OF MAMMALS AFFLICTED WITH TUMORS WITH COMPOUNDS HAVING RXR RETINOID RECEPTOR AGONIST ACTIVITY

[75] Inventors: Peter A. J. Davies, Houston, Tex.; Roshantha A. Chandraratna, Mission Viejo, Calif.

[73] Assignee: Allergan, Inc., Irvine, Calif.

[21] Appl. No.: 29,801

[22] Filed: Mar. 11, 1993

[51] Int. Cl.⁶ .................. A61K 31/38; A61K 31/19
[52] U.S. Cl. .................. 514/448; 514/438; 549/71
[58] Field of Search .............. 514/448, 438; 549/71

[56] References Cited

U.S. PATENT DOCUMENTS

| | | |
|---|---|---|
| 4,096,341 | 6/1978 | Frazer . |
| 4,326,055 | 4/1982 | Loeliger . |
| 4,391,731 | 7/1983 | Boller et al. ............ 252/299.62 |
| 4,695,649 | 9/1987 | Magami et al. . |
| 4,705,802 | 11/1987 | Lautenschlager et al. ........ 514/438 |
| 4,723,028 | 2/1988 | Shudo . |
| 4,739,098 | 4/1988 | Chandraratna . |
| 4,740,519 | 4/1988 | Shroot et al. . |
| 4,810,804 | 3/1989 | Chandraratna . |
| 4,826,969 | 5/1989 | Maignan et al. . |
| 4,855,320 | 8/1989 | Chatterjee et al. . |
| 4,895,868 | 1/1990 | Chandraratna . |
| 4,980,369 | 12/1990 | Chandraratna . |
| 4,992,468 | 2/1991 | Chandraratna . |
| 4,994,491 | 2/1991 | Purcell et al. ............ 514/448 |
| 5,006,550 | 4/1991 | Chandraratna . |
| 5,013,744 | 5/1991 | Chandraratna . |
| 5,015,658 | 5/1991 | Chandraratna . |
| 5,023,341 | 6/1991 | Chandraratna . |
| 5,037,825 | 8/1991 | Klaus et al. ............ 514/233.8 |
| 5,045,551 | 9/1991 | Chandraratna . |
| 5,049,584 | 9/1991 | Purcell et al. ............ 514/448 |
| 5,053,523 | 10/1991 | Chandraratna . |
| 5,068,252 | 11/1991 | Chandraratna . |
| 5,089,509 | 2/1992 | Chandraratna . |
| 5,130,335 | 7/1992 | Chandraratna . |
| 5,134,159 | 7/1992 | Chandraratna . |
| 5,162,546 | 11/1992 | Chandraratna ............ 549/23 |
| 5,175,185 | 12/1992 | Chandraratna ............ 514/445 |
| 5,183,827 | 2/1993 | Chandraratna ............ 514/444 |
| 5,202,471 | 4/1993 | Chandraratna ............ 562/473 |

FOREIGN PATENT DOCUMENTS

| | | |
|---|---|---|
| 0130795 | 1/1985 | European Pat. Off. . |
| 176034A | 4/1986 | European Pat. Off. . |
| 0210929 | 2/1987 | European Pat. Off. . |
| 0253302 | 1/1988 | European Pat. Off. . |
| 0284288 | 9/1988 | European Pat. Off. . |
| 0350846 | 7/1989 | European Pat. Off. . |
| 2599027 | 11/1987 | France . |
| 3708060 | 9/1987 | Germany . |
| 193990 | 7/1990 | Japan ............ 549/71 |
| 9321146 | 10/1993 | WIPO . |

OTHER PUBLICATIONS

Ursula M. Ney, et al. "Anti-Inflammatory Effects of Synthetic Retinoids May Be Related to their Immunomodulatory Action", *Dermatologica* (Suppl. 1), vol. 175, 1987, pp. 93–99.

(List continued on next page.)

*Primary Examiner*—Joseph E. Evans
*Attorney, Agent, or Firm*—Gabor L. Szekeres; Robert J. Baran; Martin A. Voet

[57] ABSTRACT

Retinoid-like compounds which act as agonists of the RXR retinoid receptor sites induce apoptosis of tumor cells in cell cultures, and are used as drugs to treat tumors in mammals including humans. Compounds which are specific agonists of RXR receptors and also compounds which are agonists of both RAR and RXR agonist (pan-agonists) induce apoptosis, although the RXR agonist compounds are preferred as drugs to avoid undesirable side effects associated with RAR agonist activity. The RXR agonists compounds are administered to mammals afflicted with tumors in pharmaceutical compositions adapted for systemic topical or for intralesional administration. The range of concentration of the active ingredient RXR agonist compound in the pharmaceutical compositions is approximately between 0.001 and 5 percent by weight, and such that the composition delivers approximately 0.1 mg to 100 mg of the active ingredient per kg body weight of the patient, per day of treatment.

22 Claims, 7 Drawing Sheets

OTHER PUBLICATIONS

A General Synthesis of Terminal and Internal Arylalkynes by the Palladium–Catalyzed Reaction of Alkynylzinc Reagents with Aryl Halides by Anthony O. King and Ei-ichi Negishi, *J. Org. Chem.* 43 No. 2, (1978) p. 358.

Conversion of Methyl Ketones into Terminal Acetylenes and (E)-Tri-substituted Olefins of Terpenoid Origin by Ei-ichi, Anthony O. King, and William L. Klima, *J. Org. Chem.* 45 No. 12, (1980) p. 2526.

Sporn et. al. in *J. Amer. Acad. Derm.* 15:756–764 (1986).
A Convenient Synthesis of Ethynylarenes and Diethynylarenes by S. Takahashi, Y. Kuroyama, K. Sonogashira, N. Hagihara, *Synthesis* (1980) pp. 627–630.

Shudo et al. in *Chem. Phar. Bull.* 33:404–407 (1985).

Kagechika et. al. in *J. Med. Chem.* 31:2182–2192 (1988).
Chemistry and Biology of Synthetic Retinoids by Marcia I. Dawson and William H. Okamura, published by CRC Press Inc., (1990), pp. 334–335, 354.

Synthesis of 2,2′-Diacyl-1,1′-biaryls. Regiocontrolled Protection of . . . by Mervic, et al, *J. Org. Chem.*, No. 45, pp. 4720–4725, (1980).

A Dopamine Receptor Model and Its Application in the Design of a New Class of Rigid Pyrrolo[2,3-g]isoquinoline Antipsychotics, Gary L. Olson, et al. *American Chemical Society*, 1981, Vo. 24, No. 9, pp. 1026–1031.

6.2.3 Conformational Restriction, Williams, et al., *Drug Discovery and Development*, (1987) The Humana Press, pp. 54–55.

V. Retinoid Structure–Biological Activity Relationships, Chemistry and Biology of Synthetic Retinoids, pp. 324–356 (1990).

Davis et al. *J. Organomettalic Chem* 387 (1990) 381–390.

Nuclear receptor that identifies a novel retinoic acid response pathway, David J. Mangelsdorf, et al., *Nature*, vol. 345, 17 May (1990), pp. 224–229.

A Retinoic Acid–responsive Element in the Apolipoprotein AI Gene Distinguishes between Two Different Retinoic Acid Response Pathways J. N. Rottman et al., *Molecular and Cellular Biology*, Jul. 1991, pp. 3814–3820.

A human retinoic acid receptor which belongs to the family of nuclear receptors, M. Petkovich, et al., *Nature*, vol. 330, 3 Dec. 1987, pp. 444–450.

Identification of a receptor for the morphogen retinoic acid, V. Giguere, et al., *Nature*, vol. 330, 17 Dec. 1987, pp. 624–629.

Identification of a second human retinoic acid receptor, Nigel Brand, et al., *Nature*, vol. 332, 28 Apr. 1988, pp. 850–853.

A third human retinoic acid receptor, hRAR- , A. Krust, et al., Proc. Nat'l. Acad, Sci, USA, vol. 86, Jul. 1989, pp. 5310–5314.

Characterization of three RXR genes that mediate the action of 9-cis retinoic acid, D. J. Mangelsdorft, et al., *Genes & Devlopment*, vol. 6, (1992), pp. 329–344.

Effects of 13-Cis-Retinoic Acid, All-Trans-Retinoic Acid, and Acitretin on the Proliferation, Lipid Synthesis and Keratin Expression of Cultured Human Sebocytes In Vitro, C. C. Zouboulis, *The Journal of Investigative Dermatology, Inc.*, vol. 96, No. 5, 5 May 1991, pp. 792–797.

Organ maintenance of human sebaceous glands: in vitro effects of 13-cis retinoic acid and testosterone, John Ridden, et al., *Journal of Cell Science*, vol. 95, (1990), pp. 125–136.

Characterization of Human Sebaceous Cells In Vitro, T. I. Doran, et al., *The Journal of Investigative Dermatology*, vol. 96, No. 3, Mar. 1991, pp. 341–348.

Retinoids as Generalized Regulators of Cellular Growth and Differentiation Peter J. A. Davies, et al., *The American Journal of the Medical Sciences*, vol. 296, No. 3, Sep. 1988, pp. 164–170.

The Molecular Basis of Retinoic Acid Action, E. Antonio Chiocca, *The Journal of Biological Chemistry*, vol. 263, No. 23, Aug. 15, 1988, pp. 11584–11589.

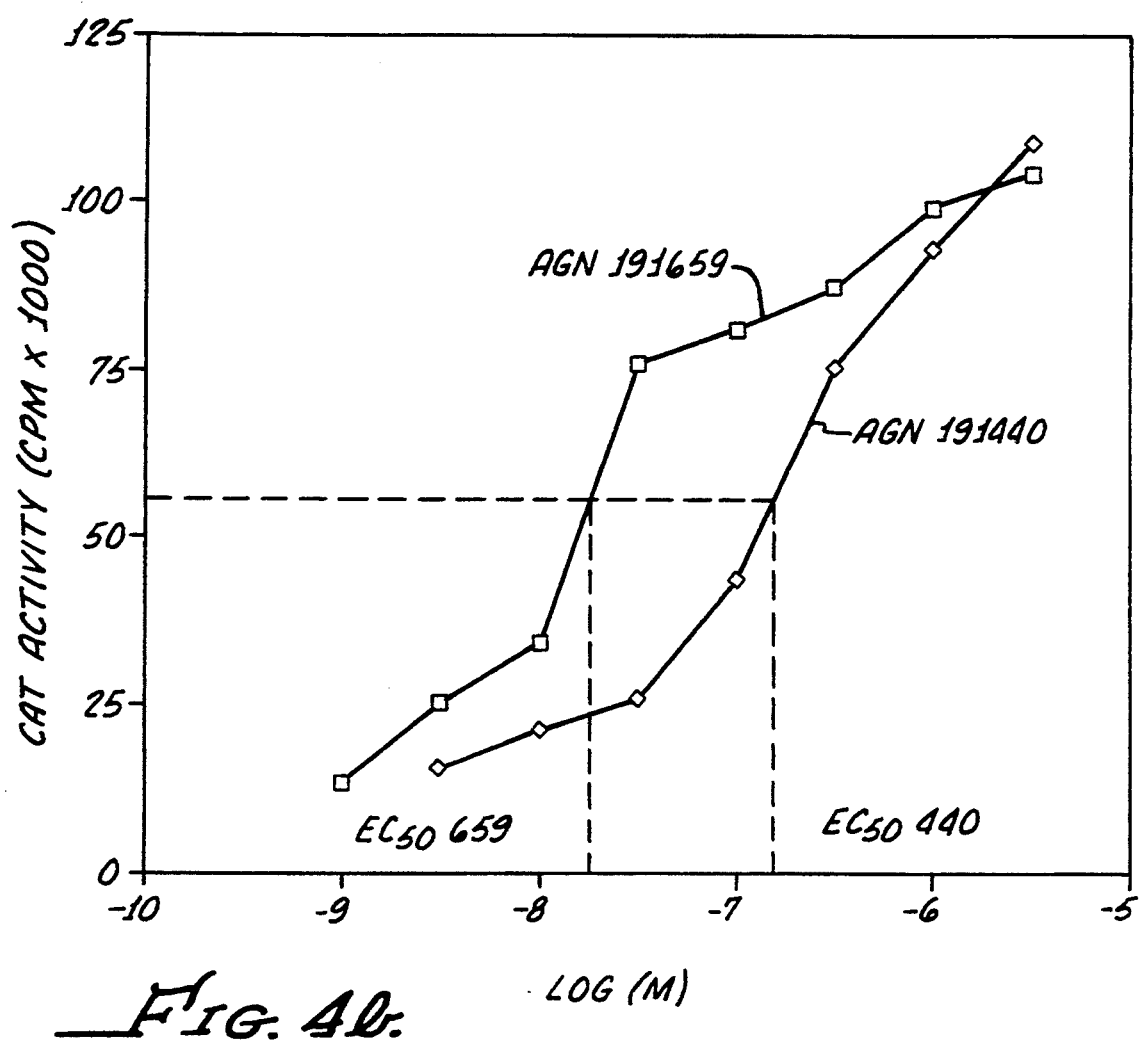
_FIG. 4b._
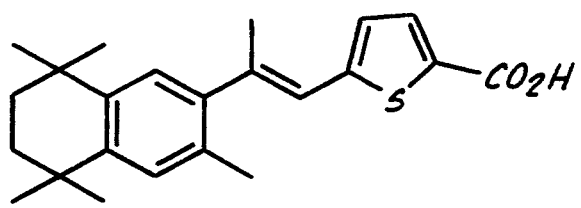
_FIG. 4a._

TREATMENT OF MAMMALS AFFLICTED WITH TUMORS WITH COMPOUNDS HAVING RXR RETINOID RECEPTOR AGONIST ACTIVITY

1. Field of the Invention

The present invention is directed to a process for inducing apoptosis in tumor cells by administration of compounds having agonist-like activity at RXR retinoid receptor sites. More specifically, the present invention is directed to a method of treating mammals suffering from tumors with RXR agonist compounds.

2. Brief Description of the Prior Art

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions such as dermatoses, acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

The compounds developed in the prior art with retinoid like properties, are, however, not without disadvantages. Several such prior art compounds cause serious irritation when applied to the skin (which is an important mode of application for treatment of skin conditions) and cause mucotaneous toxicity when administered orally as well. Many of the prior art compounds having retinoid like activity are teratogenic and have still other side effects.

In addition to numerous prior art patents and publications which describe specific compounds or classes of compounds of retinoid like activity, several co-pending applications and recently issued patents which are assigned to the assignee of the present application, are directed to further compounds having retinoid like activity and/or to methods of treatment of mammals including humans with retinoid-like compounds.

Relatively recently it was recognized in the prior art that there is more than one retinoid cellular response pathway in biological systems, and that at least two main families of receptors exist in biological systems for naturally occurring retinoid hormones. These relatively recent developments in the prior art are described in the articles: D. J. Mangelsdorf et al. "Nuclear receptor that identifies a novel retinoic acid response pathway", Nature Vol 345 May 17, 1990 pp 224–229; and J. N. Rottman et al. A Retinoic Acid-responsive Element in the Apolipoprotein AI Gene Distinguishes between Two Different Retinoic Acid Response Pathways, Molecular and Cellular Biology, July 1991, pp 3314–3820. The following additional references relate to retinoic acid receptors. M. Petkovich et al. "A human retinoic acid receptor which belongs to the family of nuclear receptor", Nature, Vol. 330, Dec. 3, 1987, pp 444–450; V. Giguere et al. "identification of a receptor for the morphogen retinoic acid", Nature, Vol 330, Dec. 17, 1987, pp 624–629; N. Brand et al. "Identification of a second human retinoic acid receptor", Nature, Vol 332, Apr. 28, 1988, pp 850–853; A. Krast et al., "A third human retinoic acid receptor, hRAR", Proc. Nat'l Acad. Sci. USA, Vol 86, July 1989, pp 5310–5314; D. J. Mangelsdorf et al., "Characterization of three RXR genes that mediate the action of 9-cis-retinoic acid", Genes & Development, Vol. 6, 1992, pp. 329–344.

The two main families of retinoid receptors are termed RAR (Retinoic Acid Receptor) and RXR (Retinoid X Receptor) in the art, and each of these two families is known to have subtype:s, which are designated by letters of the Greek alphabet, such as $RAR_\alpha$, $RAR_\beta$ and $RAR_\gamma$. The above-noted article by D. J. Mangelsdorf et al, states that some retinoid-like compounds (retinoic acid analogues) activated the RAR receptors much more strongly than the RXR receptors.

SUMMARY OF THE INVENTION

It has been discovered in accordance with the present invention that retinoid-like compounds which act as agonists of the RXR retinoid receptor sites induce apoptosis of tumor cells in cell cultures, and are therefore suitable for use as drugs to bring about apoptosis, of tumors in mammals, including humans. Specifically, it has been discovered in accordance with the present invention that retinoid-like compounds which are RXR specific agonists (hence not active on RAR receptor sites) induce apoptosis in tumors. Retinoid-like compounds which are both RAR and RXR agonists also induce apoptosis, such compounds are termed "pan agonist" compounds. Retinoid-like compounds which are specific for RAR receptor sites (not active at the RXR receptors) have not been demonstrated to cause apoptosis in tumor cell lines, and therefore RAR specific comounds can not be used in the method of treatment of the present invention.

The RXR agonist compounds are administered in accordance with the present invention to mammals afflicted with tumors, in pharmaceutical compositions adapted for systemic, or topical administration, or for intra-lesional administration. The range of concentration of the active ingredient RXR agonist compound in the pharmeceutical compositions is approximately between 0.001 and 5 percent by weight, and such that the composition delivers approximately 0.1 mg to 100 mg of the active ingredient per kg body weight of the patient, per day of treatment.

The ability of a compound to act as an agonist of the RXR receptors can be determined in a state-of-the-art assay procedure termed "Cationic Liposome Mediated Transfection Assay" which is desribed in detail below.

BRIEF DESCRIPTION OF THE DRAWING FIGURES

FIG. 4 is a graph showing data and the calculation of EC$_{50}$, obtained in the Cationic Liposome Mediated Transfection Assay on the RXR$_\alpha$ receptor, with a test compound (AGN 191659, Compound 3), and with the reference compound AGN 191440 (Compound 2).

DETAILED DESCRIPTION OF THE INVENTION

Figure 1B:
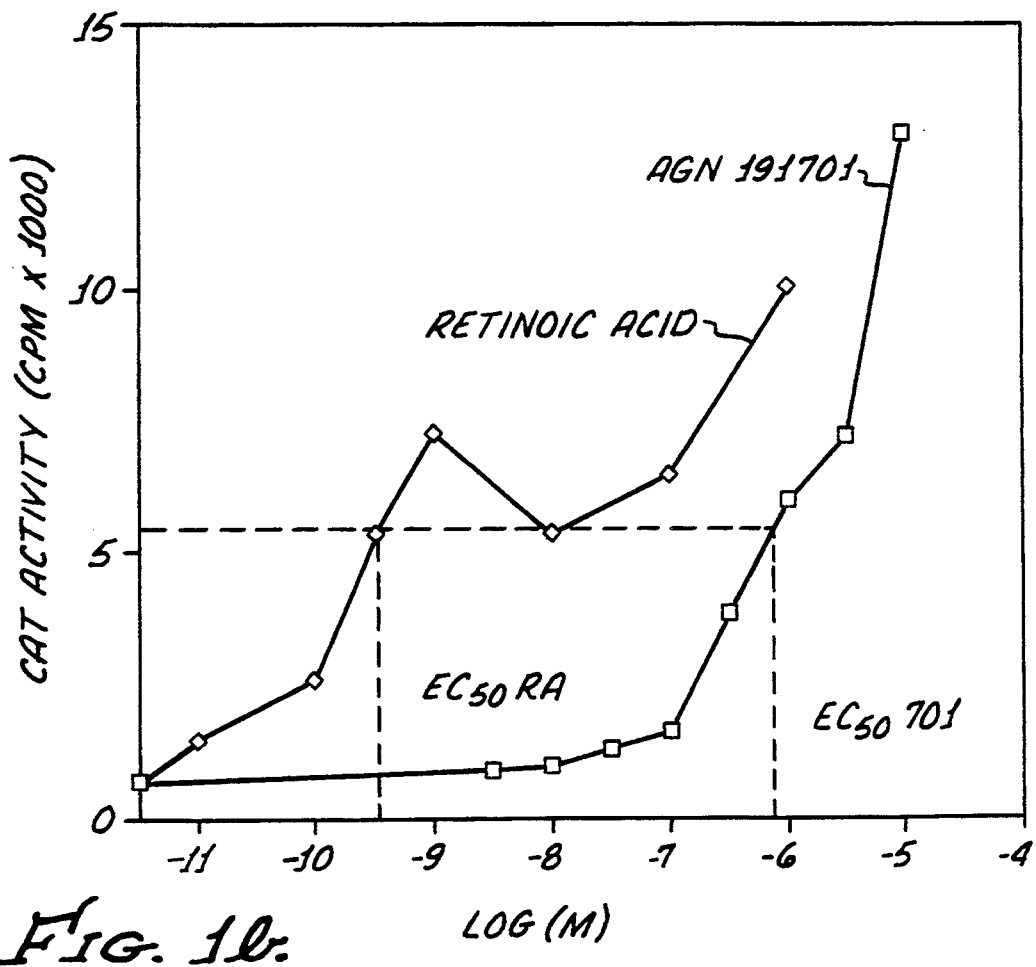
FIG. 1 is a graph showing data and the calculation of $EC_{50}$, obtained in the Cationic Liposome Mediated Transfection Assay on the $RAR_{60}$ receptor, with a test compound (AGN 191701, Compound 1), and with the reference compound trans retinoic acid.

Compounds which are used in the pharmaceutical compositions and methods of treatment of the present invention are agonists of the RXR receptor sites. Preferably for use in accordance with the method of treatment of the present invention, the compounds are specific to RXR receptors. The use of pan agonist retinoid-like compounds, which act both at RAR and RXR receptor sites is also within the scope of the present invention, although the use of pan agonist compounds is less preferred because RAR agonist activity is commonly associated with undesirable side effects. The above-mentioned Cationic Liposome Mediated Transfection Assay assay by which the activity of a test compound as a potential agonist of the RXR and RAR receptor sites is determined, is performed substantially as reported by Feigner P. L. and Holm M. (1989) Focus, 11-2, and is described below first in principle and thereafter in the form of specific instructions how to perform the assay.

In connection with this assay it is known that retinoic acid receptors arena member of the steroid/thyroid receptor super family and that they contain domains which are interchangeable within individual receptors. Thus, plasmids for chimeric retinoid receptors containing estrogen DNA binding domain and estrogen response element chloramphenicol acetyl-transferase enzyme are constructed and are grown in specific cultured bacteria. These plasmids respectively code for chimeric RAR$_\alpha$, RAR$_\beta$, RAR$_\gamma$, RXR$_\alpha$ receptor proteins, and for the chloramphenicol acetyl A transferase (CAT) enzyme protein. The bacteria with these plasmids are obtainable in accordance with the procedure set forth in the article titled "Nuclear Retinoic Acid Receptors: Cloning, Analysis, and Function", M. Pfahl et al, Methods in Enzymology 189, p 256–270 (1990) which is incorporated herein by reference. The detailed procedure how to isolate the DNA plasmids from the respective bacteria is also set forth below in detail, in the form of specific instructions under the title "Supercoiled Plasmid Isolation".

Thus, in accordance with the test procedure, DNA plasmid which codes for one of the chimeric RAR$_\alpha$, RAR$_\beta$, RAR$_\gamma$, or RXR$_\alpha$ receptor proteins is transfected into cultures of HeLa cells. It is for this purpose that HeLa cells are grown in a medium during the first day of the assay detailed below as the "Cationic Liposome Mediated Transfection Assay". In the transfection procedure, which is performed during the second day of the transfection assay, the DNA plasmid coding for the CAT enzyme is also added to each cell culture, in addition to the respective chimeric RAR$_\alpha$, or RAR$_\beta$ etc. coding plasmid. As is known and will be readily understood by those skilled in the art, especially in view of the above-cited M. Pfahl et al. article, chimeric retinoid receptors involved in this assay include a ligand binding domain which recognizes and binds specific agonist molecules, such as retinoic acid and analogs. These chimeric protein receptors (which were constructed in accordance with the teachings of the M. Pfahl. et al, article) also contain a a DNA binding domain, which is capable of binding to the "estrogen response element" (a DNA fragment) attached to the DNA plasmid coding for the CAT enzyme. The nature of the interaction is such, that only if an agonist (such as retinoic acid or analog) is bound to the ligand binding domain of the respective RAR$_\alpha$, RAR$_\beta$. etc. receptor, only then is the receptor bound through its DNA-binding domain to the estrogen response element of the estrogen-response-element-chloramphenicol-acetyl transferase-construct (ERE-CAT) capable of initiating transcription of messenger RNA for the CAT enzyme. In other words, through multiple interactions CAT enzyme is manufactured by the HeLa cell in this assay only if an appropriate agonist ligand binds to the ligand binding site of the respective retinoid receptor.

The estrogen response-element-chloramphenicol acetyl-transferase construct (ERE-CAT) is itself obtained in accordance with the procedure described in the article Ryssel G. U. et al. Cell, Volume 46, pp 1053–1061 (1986), which is incorporated herein by reference. This procedure per se is well known in the art. The specific detailed procedure how to isolate and obtain the estrogen-response-element chloramphenicol-acetyl-transferase-construct (ERE-CAT) from bacteria is descibed in the procedure titled "Supercoiled Plasmid Isolation".

In addition to the foregoing, lipofectin (LF) is also added to each cell culture. The purpose of the lipofectin is to facilitate transport of plasmids through the cell membrane. The lipofectin used in the procedure is available commercially.

As it will be well understod by those skilled in the art, as a result of transfection with the respective DNA plasmid coding for RAR$_\alpha$, or RAR$_\beta$ etc. chimeric receptors and as a result of transfection with the ERA-CAT (which codes for the CAT enzyme as described above), the aforementioned plasmids are incorporated into the HeLa cells cultured in the assay. The retinoid receptor plasmids undergo transcription (into m-RNA) and subsequent translation into the corresponding chimeric receptor protein. Therefore, the Hela cells cultures obtained in this manner manufacture the respective RAR$_\alpha$, RAR$_\beta$, RAR$_\gamma$, or RXR$_\alpha$ chimeric receptor protein. As a result of transfection with the ERA-CAT the cell cultures of this asssay also contain the genetic information for manufacturing the CAT enzyme. However, as is noted above, the latter genetic information is not transcribed, and the CAT enzyme is not manufactured by the respective cell cultures of this assay, unless an appropriate agonist compound binds to and activates the respective $RAR_\alpha$, $RAR_\beta$, RAR, or $RXR_\alpha$ chimeric receptor protein in the cell and this activated agonist-receptor complex binds to the estrogen response element of the ERE-CAT construct.

The assay procedure is continued by adding, on the third day of the assay, an appropriate reference compound and the test compound (agonist or prospective agonist) to the respective HeLa cell culture, preferably in varying concentrations. As a result of this addition, if the test compound is an agonist, it binds to the respective $RAR_\alpha$, $RAR_\beta$, $RAR_\gamma$, or $RXR_\alpha$ chimeric receptor protein, and consequently the genetic information which codes for the CAT enzyme is transcribed in the cell, whereby CAT enzyme is made by the cell.

After lysis of the cell, which is performed on the fourth day of the below-detailed assay procedure, the activity of CAT enzyme in aliquot portions of the lysate is measured. This is done by incubating the lysate with chloramphenicol and tritium labeled acetyl coenzyme A. As a final measurement, the amount of tritium labelled acetyl chloramphenicol, which is formed in the enzymatic reaction involving the CAT enzyme, is measured in a scintillation counter.

Figure 1A:
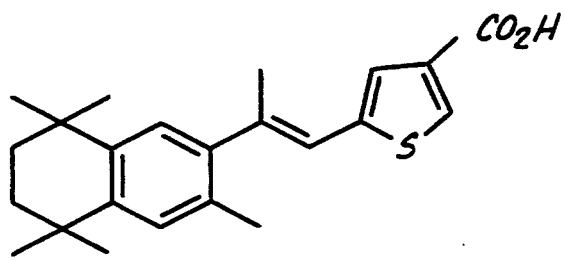
Figure 3B:
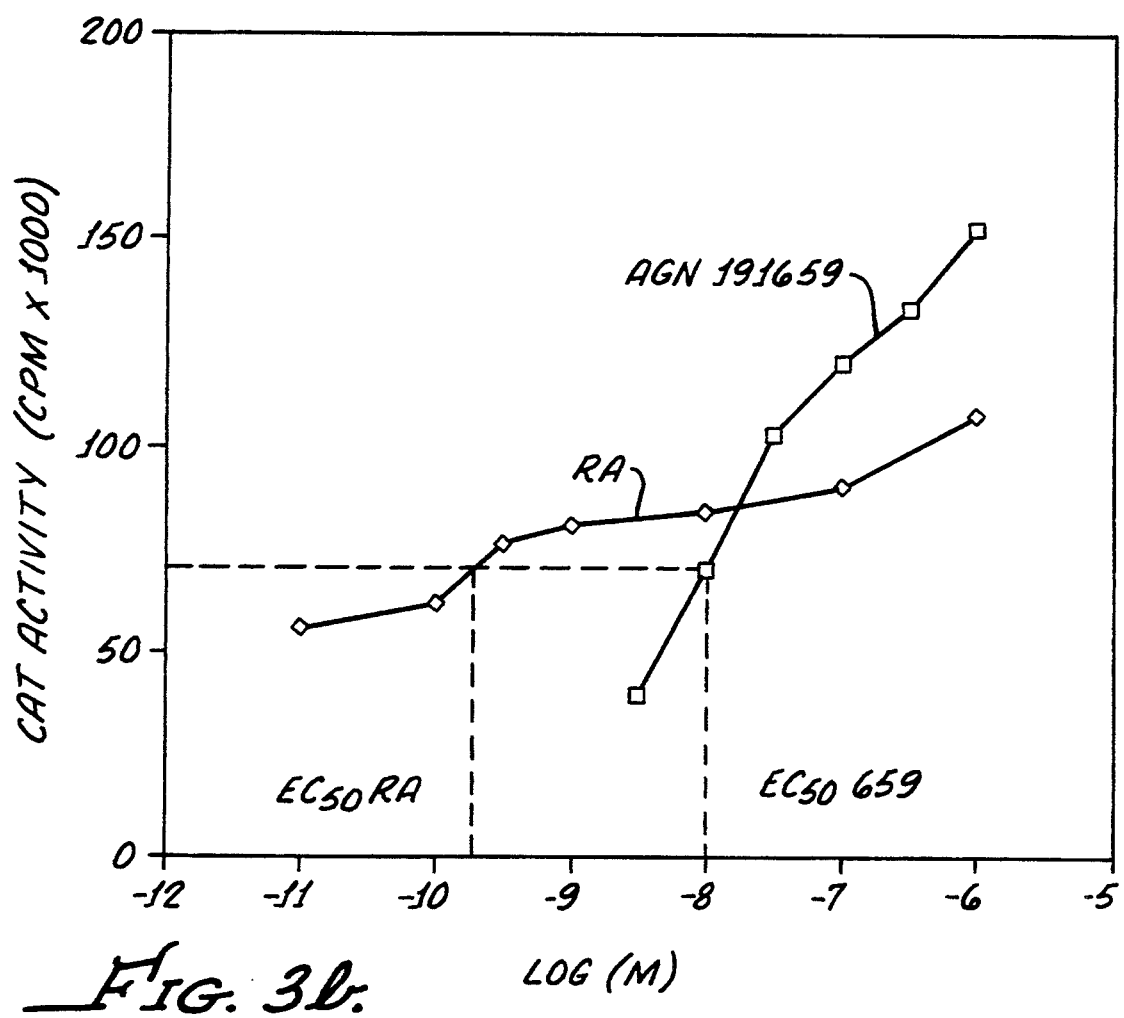
FIG. 3 is a graph showing data and the calculation of EC$_{50}$, obtained in the Cationic Liposome Mediated Transfection Assay on the RAR$_\alpha$ receptor, with a test compound (AGN 191659, Compound 3), and with the reference compound trans retinoic acid.
Figure 3A:
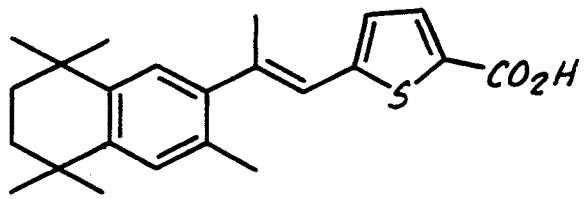

The reference compound is retinoic acid (all trans) for the assays involving the $RAR_\alpha$, $RAR_\beta$, and $RAR_\gamma$ receptors, and 4-(E)-2-(5,6,7,8-tetrahydro-3,5,5,8,8-pentamethylnaphthalen-2-yl)propen-1-yl]benzoic acid (AGN 191440, also designated Compound 2 in this application) for the $RXR_\alpha$ chimeric receptor. The data obtained in the assay are evaluated and expressed as follows. For each test compound and for each subspecies of the RAR receptors a graph (or the mathematical equivalent of a graph) is prepared where the "counts per minute" (cpm) obtained in the scintillation counter measurements are plotted (on the y axis) against the concentration of the test compound. A similar graph (or mathematical equivalent) is prepared for retinoic acid. $EC_{50}$ of the test compound is defined as that concentration of the test compound which provides ½ (50%) of the maximum cpm number (maximum CAT enzyme activity) obtained in the same receptor in the same assay with the reference compound retinoic acid. This is illustrated in the graphs of FIG. 1 and FIG. 3.

Figure 2B:
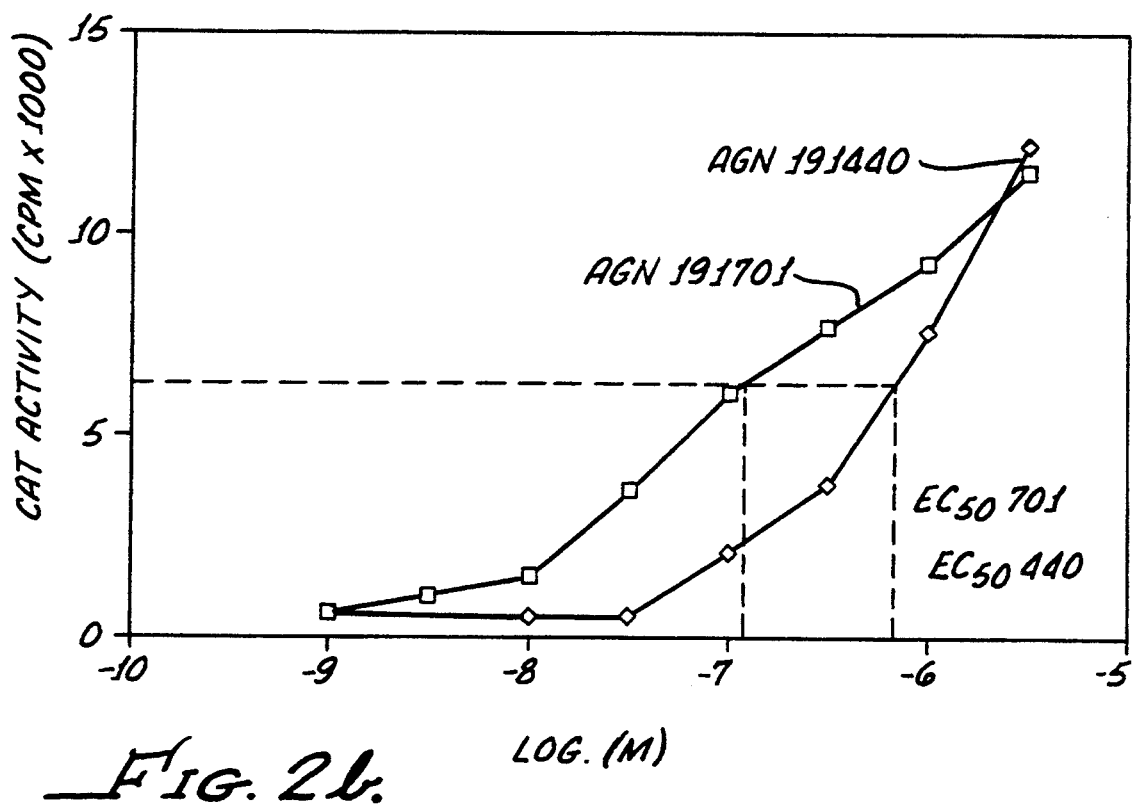
FIG. 2 is a graph showing data and the calculation of EC$_{50}$, obtained in the Cationic Liposome Mediated Transfection Assay on the RXR$_\alpha$ receptor, with a test compound (AGN 191701, Compound 1), and with the reference compound AGN 191440 (Compound 2).
Figure 2A:
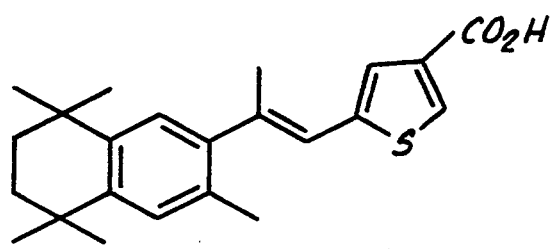

To evaluate and express the data obtained in the assay for the $RXR_\alpha$ receptor, the same type of graph (or mathematical equivalent) is prepared for the test compound, and also for the reference compound AGN 191440, Compound 2. This reference compound is a known agonist of the $RXR_\alpha$ receptor site. $EC_{50}$ is that concentration of the test compound which gives one half (50%) of the counts per minute (CAT enzyme activity) of the maximum cpm obtained with AGN 191440 on the same receptor in the same assay. A graph illustrating the foregoing is shown in FIG. 2 and FIG. 4.

SUPERCOILED PLASMID ISOLATION

Large Scale 1L Prep

DNA isolation

1. Place cells on ice for 15 minutes. Harvest the bacterial cells (*E. coli*) by spinning down in 250 ml nalgene tubes at 7k rpm, 10 minutes at 4° C. using JA14 rotor, Beckman J2-21 M centrifuge. Discard the supernatant.

2. To each cell pellet add 1.0 ml Solution I, vortex to resuspend the pellet. Transfer the 1.0 ml of cells from one bottle to another. Transfer this to a 50 ml Oakridge tube. Use 4 ml of Solution I and wash the bottles again transferring from one bottle to the next. Transfer this also into the Oakridge tube. Using a pipet bring up the total volume to 16 ml with Solution I and mix the solution. Transfer 8 ml to a second Oakridge tube. Store at room temperature for 5 minutes.

Solution I 50 mM glucose, 25 mM Tris-Cl pH 8, 10 mM EDTA pH 8

3. Add to each tube 18 ml of freshly prepared Solution II. Mix contents gently by inverting the tube several times. Store on ice for 10 minutes. After this time the liquid should be clear with no aggregates. (If there are clumps, then the cells were not resuspended well enough previously.)

Solution II

1% sodium dodecylsulfate (SDS), 0.2N NaOH (4 ml 10% SDS, 0.8 ml 10N NaOH, 35.2 ml water)

4. Add 12 ml, (or as much as will fit) of ice-cold Solution III. Mix the contents of tube by inverting it sharply several times. A white flocculent precipitate should appear. Store on ice for 10 minutes.

Solution III prepare as follows: to 60 ml 5M potassium acetate, add 11.5 ml of glacial acetic acid and 28.5 ml water.

5. Centrifuge at 4° C. in a Beckman J2-21M centrifuge, JA20 rotors, 17k rpm for 30 minutes.

6. Pipet approximately 12 ml of supernatant from the Oakridge tubes into 6 baked Corex tubes. Add 0.6 volumes of isopropanol (7.2 ml) mix by inversion and store at room temperature for 15 minutes to precipitate DNA.

7. Warm Beckman centrifuge by spinning JA20 rotor at 14k rpm for 15 minutes at 20° C.

8. Pellet DNA at 20° C. in the J2-21M centrifuge, JA20 rotor at 10.5k rpm for 30 minutes (use adapters for corex tubes).

9. Pour off supernatant, dry inside of tube with pasteur pipet on a vacuum flask.

10. Dry in vacuum dessicator for 10 minutes (Longer drying time will make it hard to dissolve pellet).

Purification of plasmid DNA by centrifugation to equilibrium in CsCl density gradients 11. Dissolve pellet by adding 1 ml TE (10 mM Tris-Cl pH 8, 1 mM EDTA pH 8) to each corex tube. Place tubes in 37° C. water bath to help pellets to dissolve faster (15–30 minutes).

12. Transfer liquid from like batch into one tube. Bring volume to 8.5 ml with TE.

13. Add 100 µl RNase, DNase free (2U/µl, source Boehringer Mannheim Biochemical (BMB)).

14. Add 400 µl of 10 mg/ml Ethidium Bromide.

15. Add 9.0 g CsCl and mix using a pasteur pipet.

16. Add solution to two 13×51 mm Beckman polyallomer quick-seal centrifuge tubes.

17. Spin at 50k rpm for 12 hours in Beckman ultracentrifuge, VTi65.2 rotor, 20° C.

18. After ultracentrifugation, two bands of DNA should be visible. The upper band consists of linear bacterial DNA and nicked circular plasmid DNA. The lower band consists of closed circular plasmid DNA. Only the lower CsCl-banded DNA is removed from the tube with a 3-ml syringe fitted to an 21-gauge needle (Needle is inserted into the side of the tube and 1.5–2 ml is removed).

19. Preparation for Second CsCl centrifugation:

(9 ml—vol 1st CsCl band)—number g CsCl
(9 ml—vol 1st band—100 µl 10 mg/ml Ethidium Bromide—50 µl RNase)—ml TE pH 8.0
Combine 1st band, TE, CsCl, RNase and EtBr.

20. Add solution to 2 quick-seal tubes.
21. Spin at 50k for 12 hours or 60k rpm for 4 hours in ultracentrifuge, VTi65.2 rotor, 20° C.
22. Remove twice CsCl-banded DNA (lower band only) to a 5 ml Falcon snap tube (as in step 18).

Extraction of ethidium bromide

23. Under fumehood add an equal volume isoamyl alcohol, vortex, spin at room temperature at 1500 rpm in Beckman TJ-6 centrifuge for 3 minutes.
24. Transfer bottom aqueous layer to fresh tube. Repeat 3–4 times or until aqueous layer is clear (no pink color).
25. Transfer clear aqueous layer to Spectra/Por 3 dialysis tubing, mwco 3500, (Tie a knot in the bottom of tubing before clamping dialysis tubing.) Add liquid using a pasteur pipet. Clamp top or dialysis tubing. Using a rubber band suspend tubing in 2.8 L TE (28 ml 1M Tris-Cl, pH 8, 5.6 ml 0.500M EDTA, pH 8). Always handle dialysis tubing carefully, with gloves.
26. Dialyze aqueous phase against several changes of 2.8L TE pH 8 (1×2–4 hours, overnight and 1×2–4 hours the next day).
27. In the tissue culture hood transfer the dialyzed DNA into sterile microcentrifuge tubes. Label tubes and store at −20° C.

CATIONIC LIPOSOME-MEDIATED TRANSFECTION

Reference: Felgner, P. L., and Holm, M. (1989) Focus 11, 2.

USE STERILE TECHNIQUE THROUGHOUT

Grow up HeLa or CV-1 cells in T-125 culture flask. Cells are passed twice a week usually on Monday and Friday (0.5 ml cells into 15 ml medium)

Day 1: Plating cells

1. Trypsinize and collect cells from T-162 $cm^2$ culture flask. Count cells using a hemocytometer. Usually, this amount of cells is enough for sixteen 12-well plates.
2. Based on the cell number, dilute cells in medium (D-MEM low glucose, 10% fetal bovine serum (FBS), 2 mM Glu) to a concentration of 60,000 cells per well.

Example cell calculation:
want 40,000 cells/well and 200 wells
have (X) cells/ml
therefore, $$\frac{40{,}000 \text{ cells/well}}{(X) \text{ cells/ml}} \times 200 \text{ wells} = \text{total \# ml cells needed}$$

Using a Nalge 250 ml Filter Unit Receiver add total # ml cells to medium and bring final volume to 200 ml. Mix well by pipetting.

3. Add 1.0 ml of cells per well using a sterile 12.5 ml combitip (setting 4). Shake plates back and forth (do not swirl). Incubate at 37° C. in a humidified 5% $CO_2$ environment overnight. Cells are about 40% confluent prior to transfection.

Transfection: Day 2 Preparation DNA/Lipofectin Complex

1. Using 50 ml polystyrene tubes prepare Lipofectin (LF) and DNA separately. Determine vol of LF and DNA needed for 2 µg LF/well, 500 ng ERE-CAT DNA/well, 100 ng ER/RAR DNA per well. Determine total volume needed for experiment. (DNA concentration will vary between each plasmid prep and the following calculations will need to be adjusted accordingly.)

| DNA (prep date) | µl/well | #wells | vol DNA | Vol Opti-Mem |
|---|---|---|---|---|
| α | | | | |
| β | | | | |
| τ | | | | |
| X | | | | |
| CAT | | | | |
| LP lot # | µl/well | #wells | µl LF | Vol Opti-Mem |

Separately dilute LF and DNA in Opti-Mem media to a volume of 25 ul×# wells: Vol Opti-Mem 1=(25 ul×# wells)−total vol. DNA or LF.

2. Add the diluted LF to the diluted DNA and swirl tube gently. Let sit room temperature for 10 min.
3. Aspirate off the medium from the wells and wash 2× using 0.5 ml Opti-Mem I (sterile 12.5 ml combitip, setting 2).
4. Add the DNA/LF complex to vol of Opti-Mem: (450 µl× # wells). Invert tube to mix. Using a sterile 12.5 ml combitip (setting 2) add 500 µl to each well. Shake plates back and forth to mix, do not swirl.
5. Incubate the cells for 6 hours at 37° C. in a humidified 5% $CO_2$ incubator.
6. After 6 hours add 0.5 ml medium to each well (D-MEM low glucose, 20% FBS charcoal treated, 2 mM Glu) Use 12.5 combitip setting 2 and place back in the incubator.

Day 3: Drug addition 1. 18 hours after the start of transfection add retinoids in triplicate (10 µl) using a sterile 0.5 ml combitip (setting 1) and incubate for 20–24 hours at 37° C. in a humidified 5% $CO_2$ environment.

DRUG DILUTIONS $$\frac{\text{weight (g)}}{\text{ACETONE mol. wt (g/mol)}} \times \frac{1}{.005 \text{ mol/L}} \times \frac{100 \text{ mol}}{L} = \underline{\phantom{ml}} \text{ ml}$$

Example: Retinoids are dissolved in acetone to a conc. of 5 mM and further diluted to 1 mM in EtOH. If retinoids do not go into solution place tube in hot water for 5 seconds followed by vigorous vortexing. Each experiment may have a different dilution scheme. For 2 concentrations per order of magnitude use a 3.16-fold dilution as follows: To labeled sterile 12×75 mm tubes (Falcon 2063) add 1080 ul of 100% EtOH. Using the 1 mM solution transfer 500 ul to the next tube (316 µM). Vortex and repeat the transfer to the next tube down the line . . . Some retinoids are light sensitive, especially RA and 13-cis RA, and should be used with a red or very dim light. Log in the amount of compound used.

Example

| Drug Dilution | Vol add to well | Final: −log [conc.] |
|---|---|---|
| 5 mM (initial) | | |
| 1 mM | 10 | 5.0 |
| 316 µM | 10 | 5.5 |
| 100 µM | 10 | 6.0 |
| 31.6 µM | 10 | 6.5 |
| 10 µM | 10 | 7.0 |
| 3.16 µM | 10 | 7.5 |
| 1 µM | 10 | 8.0 |
| 316 nM | 10 | 8.5 |
| 100 nM | 10 | 9.0 |
| 31.6 nM | 10 | 9.5 |

-continued

| Drug Dilution | Vol add to well | Final: −log [conc.] |
|---|---|---|
| 10 nM | 10 | 10.0 |
| 3.16 nM | 10 | 10.5 |
| 1.0 nM | 10 | 11.0 |

Day 4 Mixed Phase CAT Assay

1. Wash cells in 12 mm wells once with 0.50 ml 1×PBS (no Ca/Mg).
2. Using a 5 ml combipipet (setting 1) add 100 μl of a ice cold 1% Triton, 1 mM Tris-Cl pH 7.8, 2 mM EDTA pH 8, DNase I. Prepared as follows:

| LYSIS BUFFER (hypotonic buffer) |
|---|
| 2.0 mg DNase I (Sigma) |
| 4.925 ml water |
| 50.0 μl 100% Triton X-100 (BMB Lot # |
| 5.0 μl 1M Tris-Cl pH 7.8 |
| 20.0 μl 0.5M EDTA pH 8 |
| 5.0 ml |

3. Place on ice for 60 minutes. Agitate occasionally.
4. Transfer 50 μl lysate from 3 wells at a time using titertrek multichannel pipet with tips attached to channels #1, #3, #6 to 96 U-bottom well (Costar). Place (unused lysate) plates at −20° C.
5. Using a 1.25 ml combipipet (setting 1) add 50 μl premix per well, gently shake plates and incubate 37° C. for 2 hours.

| Vol. per Blank | Vol per reaction X__ (#assays) = total vol. |
|---|---|
| 47.0 | 27.0 μl buffer I (250 mM Tris-Cl pH 7.8, 5 mM EDTA (Date: |
| 1.5 | 1.5 μl 1 mM HCl |
| *** | 20.0 μl 5 mM Chloramphenicol (make fresh in buffer I) Lot# |
| 0.75 | 0.75 μl 4 mM Acetyl CoA in water (make fresh) Sigma Lot# |
| 0.80 | 0.80 μl 3H-Acetyl CoA (New England Nuclear) #NET-290L, 200mCi/mmol) |

6. Using a titertrek multichannel pipet add 100 μl of 7M Urea into each reaction well to quench the reaction. Do six at a time (Urea-Mallincrokt AR)
7. Using a titertrek multichannel pipet transfer 200 μl reaction mixture into a 5 ml plastic scintillation vial (Research Products International #125514). Do three reactions at a time. (Urea-Mallincrokt AR)
8. Add 1 ml 0.8% PPO/Toluene (3.2 g PPO/4L Toluene) Vortex vigorously for 5 seconds and allow the phases to separate for 15 minutes. Count cpm for 2.0 min-Beckman LS 3801. (Toluene-Mallinckrodt Scintil-1AR) (PPO=2,5 Diphenyloxazole-RPI Lot #A3071

Table 1 illustrates the comparative RAR and RXR agonist activity of two specific examplary compounds in accordance with the invention. Compound 1, (AGN 191701) is 2-[(E)-2-(5,6,7,8-tetrahydro-3,5,5,8,8-pentamethylnaphthalen- 2-yl)propen-1-yl]thiophene-4-carboxylic acid. Compound 2 (AGN 191440) is the reference compound for measuring RXR agonist activity, this compound is 4-(E)-2-(5,6,7,8-tetrahydro-3,5,5,8,8-pentamethylnaphthalen-2-yl)propen-1-yl]benzoic acid. Compound 3 (AGN 191659) is 2-[(E)-2-(5,6,7,8-tetrahydro-3,5,5,8,8-pentamethylnaphthalen-2-yl)propen-1-yl]-5-thiophenecarboxylic acid. The activity of the examplary compounds in accordance with the invention, is indicated separately for the respective $RAR_\alpha$, $RAR_\beta$ and RAR receptor sites. The structure of each compound indicated in Table 1 is provided in the description below. Compound 4 (AGN 191183) is 4-(E)-2-(5,6,7,8-tetrahydro-5,5,8,8-tetramethylnaphthalen-2-yl)propen-1-yl]benzoic acid. This compound (Compound 4) is not within the scope of the invention. Receptor data for this compound are provided for the sake of comparison, to show that this compound is a specific RAR agonist, and not active at RXR receptor sites. In accordance with the present invention Compound 4 is not active in the assay where apoptotic death of tumor cells upon treatment with RXR agonist compounds is demonstrated.

TABLE 1

| Compound # | $EC_{50}$ | | | |
|---|---|---|---|---|
| | $RAR_\alpha$ | $RAR_\beta$ | $RAR_\gamma$ | $RXR_\alpha$ |
| 1 | NA | 3349 | 1073 | 67 |
| 2 | 3160 | 101 | 364 | 448 |
| 3 | >>1000 | 23 | 153 | 11.2 |
| 4 (AGN 191183) | 19 | 1.0 | 0.3 | >10,000 |

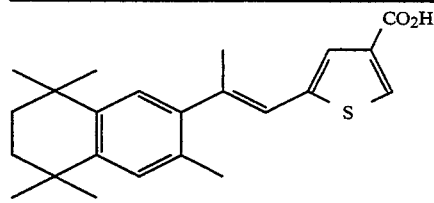

Compound 1, (AGN 191701)

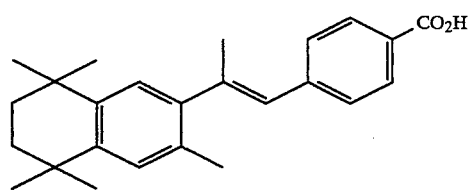

Compound 2 (AGN 191440)

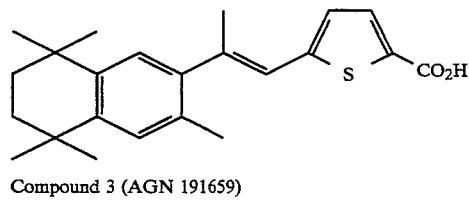

Compound 3 (AGN 191659)

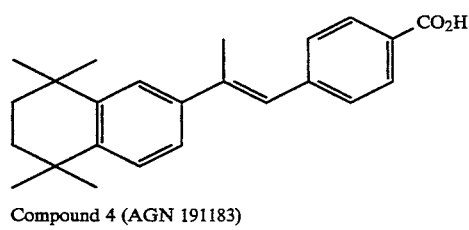

Compound 4 (AGN 191183)

The phenomenon of apoptosis is well known in the biological sciences and can be described as a programmed death of cells. As is known, apoptosis is contrasted with "necrosis", a phenomenon when cells die as a result of being killed by a toxic material, or other external effect. Apoptosis, is thus a "natural", programmed death of cells. Along these lines, it is generally known that even in a growing malignant tumor which is possibly life-threatening to the host, a large number of cells naturally die by apoptosis. However, in a normally growing malignant tumor (unaffected by successful chemotherapy or other treatment) the number of new cells formed by uncontrolled cell division exceeds the number of cells which die by apoptosis, so that the tumor gains anet increase in size. If the rate of death by apoptosis in the tumor were to exceed the rate of cell division, the tumor would shrink or disappear altogether. In accordance with the present invention and discovery the ability of RXR agonist compounds to induce apoptotic cell death is demonstrated in an assay which utilizes the phenotype of a line of human myeloid leukemia (HL-60 cdm1-1) cells.

In the assay, the human myeloid leukemia (HL-60 cdm1-1) cells are grown in cultures, and an RXR agonist compound, such as Compound 1 (AGN 191701) or Compound 3 (AGN 191659), is added to the culture. The RAR specific Compound 4 (AGN 191183) is added to parallel cultures for control, while other "control" cultures are treated with ethanol. The assays showed that the RXR agonist compounds (but not the RAR specific Compound 4 (AGN 191183) nor ethanol) induced significant apoptotic cell death. The apoptotic nature of the cell death was demonstrated by the observed morphological changes (nuclear pyknosis and fragmentation), membrane blebbing and cellular fragmentation, and by the characteristic laddering of DNA fragments in the treated cells.

A detailed description of the assays is provided below.

Assays Demonstrating Induction of Apoptosis in Human Myeloid Leukemia (HL-60) Cells by RXR Agonist Compounds (AGN 191701)

Assay 1

HL-60 cdm-1 cells were plated into 6-well tissue culture plates (Falcon) in 3 ml of media (RPMI-1640 containing bovine insulin 5 mg/L, human transferrin 5 mg/L and Na Selenite 5 $\mu$g/L at a density of $1 \times 10^{+5}$ cells/ml. Three $\mu$l of a 1 mM stock solution of AGN 191701 (Compound 1) or 1 mM", of AGN 191183 (Compound 4) or ethanol was added to the cells and then the cells were cultured in a humidified incubator (5% $CO_2$) at 37° C. in the dark for 72 hours. At the end of the incubation, aliquots of the cells were taken for counting in a hemocytometer chamber and a second aliquot, (50 $\mu$l), was sedimented onto a microscope slide using a cytospin centrifuge. Sedimented cells were air dried, fixed in absolute methanol, stained with a Diffquick reagent kit, mounted in Permount and visualized by brightfield light microscopy.

Cell counts were as follows:

| Control | $5.1 \times 10^{+5}$ / ml |
|---|---|
| AGN 191183 (1 uM) | $4.6 \times 10^5$ / ml |
| AGN 191701 (1 uM) | $0.7 \times 10^5$ / ml |

Inspection of the microscope slides revealed no difference between the control and the AGN 191183 (Compound 4)-treated cells. The AGN 191701-treated cells showed extensive cell death, almost all cells died.

Assay 2

HL-60 cdm-1 cells were placed in a T-25 tissue culture flask in 8 ml of media (RPMI-1640 containing bovine insulin 5 mg/L, human transferin 5 mg/L and Na Selenite 5 $\mu$g/L) at a density of $2 \times 10^5$ cells/ml. AGN 191701 (Compound 1) was added to a final concentration of 1 $\mu$M (8 $\mu$l of a 1 mM stock solution) and the cells were cultured in a humidified incubator (5% $CO_2$) at 37° C. in the dark for 48 hours. The media and cells were removed from the flask, the cells were pelleted (1100 rpm/7 min Beckman desk top centrifuge), the pellet was washed once with phosphate buffered saline (PBS) and then the pelleted cells were lysed by the addition of 200 $\mu$l of a solution containing 20 mM Tris-HCl pH 7.4, 0.4 mM EDTA, 0.4% Triton X-100. The lysate was centrifuged for 5 minutes in a microfuge (14,000 rpm) and the supernatant adjusted to a final concentration of 0.5M NaCl and 50% isopropanol. The solution was allowed to precipitate overnight at $-20°$ C. and the precipitate that formed was pelleted in a microfuge (10 min, 14,000 rpm). The pellet was washed once in 70% ethanol, it was resuspended in 50 $\mu$l Tris EDTA (10 mM Tris HCl ph 7.4, 0.4 mM EDTA) and mixed with gel loading buffer. The sample was electrophoresed for 1 hour in a 1% agarose gel alongside a 1 kB standard DNA ladder (Bethesda Research Laboratory). DNA was detected by ethidium bromide staining followed by visualization and photography under a UV lamp.

Inspection of the DNA demonstrated a pattern of DNA fragmentation ("laddering") characteristic of cells undergoing apoptotic cell death., Assay 3

HL-60 cdm-1 cells were plated in a 6-well tissue culture plate (Falcon) in 3 ml of media (RPMI-1640 containing bovine insulin 5 mg/L, human transferrin 5 mg/L and Na Selenite 5 $\mu$g/L) at a density of $1 \times 10^5$ cells/ml. Duplicate wells received either ethanol (3 $\mu$l) or 3 $\mu$l of a stock solution of AGN 191701 (Compound 1, 1 mM in ethanol). The cells were cultured in a humidified incubator (5% $CO_2$) at 37° C. in the dark for either 4 hours, 48 hours or 6 days. At the indicated times an aliquot of the cells (50 $\mu$l) was sedimented onto a microscope slide using a cytospin centrifuge. Sedimented cells were air dried, fixed in absolute methanol, stained with a Diffquick reagent kit, mounted in permount and visualized by brightfield light microscopy.

Inspection of the cells revealed that the control cells are numerous undifferentiated blastic myeloid leukemia cells. Cells exposed to AGN 191701 (Compound 1) for 4 hours showed nuclear pyknosis and nuclear as well as cytoplasmic hyperchromicity with the formation of cytoplasmic extensions (large blobs). At 48 hours there was extensive cell death with numerous hyperchromatic nuclear fragments either free in the media or contained with shrunken cell remnants. There is a small residual population of blastic undifferentiated cells. After 6 days the same hyperchromatic nuclear remnants are detected but in addition there are scattered multinucleated syncitial cells ("giant cells") present in the culture. The pattern of morphologic changes in the dying cells are entirely consistent with the changes described in cells undergoing apoptotic cell death.

Figure 5:
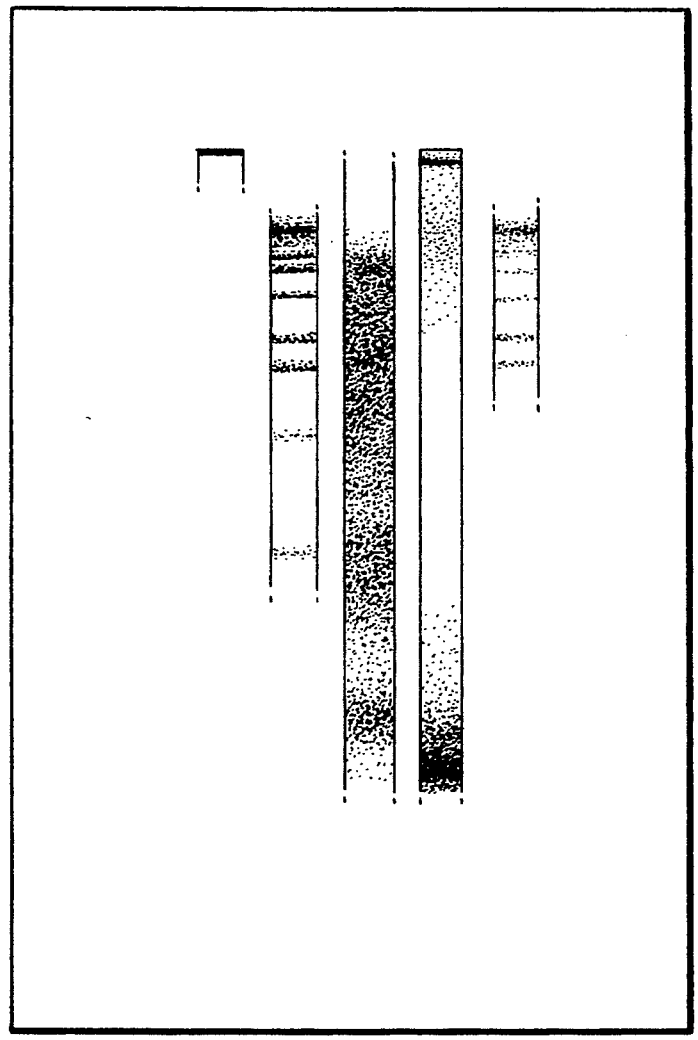
FIG. 5 is a photograph of a DNA "ladder" obtained from HL-60 cdm-1 cells which had been treated with Compound 1 (AGN 191701).
Figure 6:
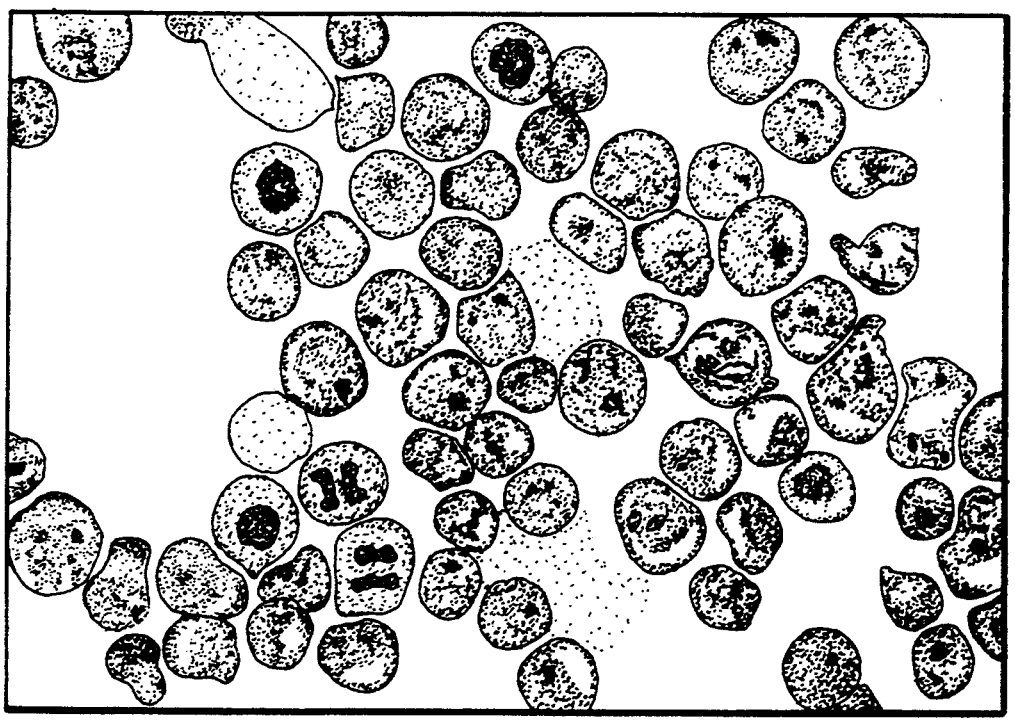
FIG. 6 is a photograph of "control" cells which have been treated with "media" but not with an RXR agonist compound in accordance with the invention.
Figure 7:
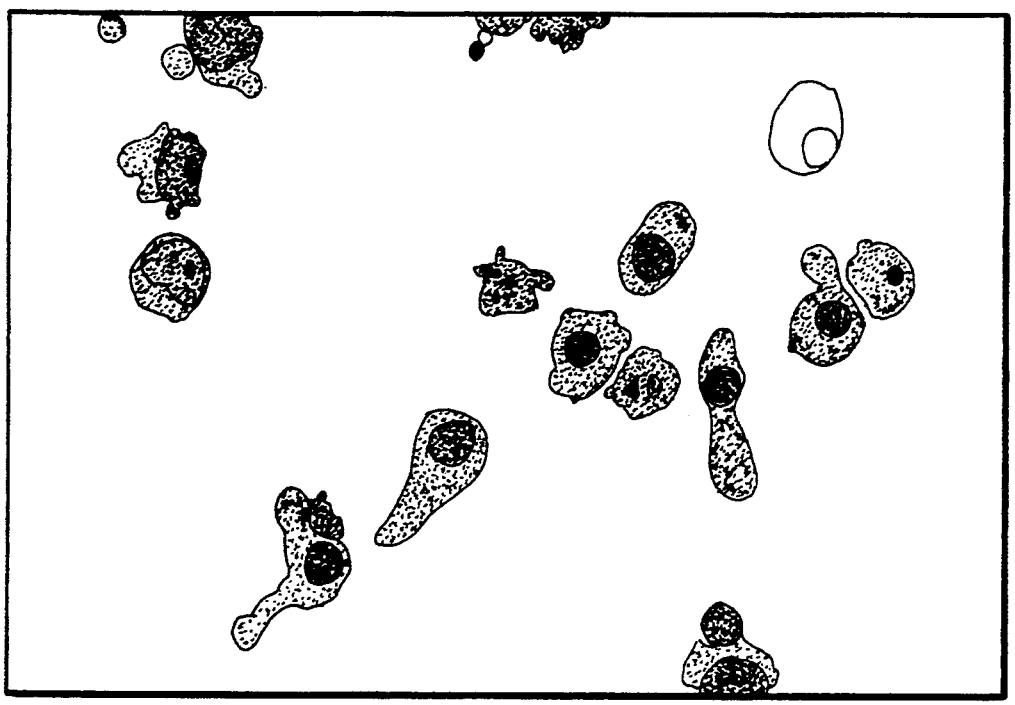
FIG. 7 is photograph of cells which have been treated for 4 hours with Compound 1.
Figure 8:
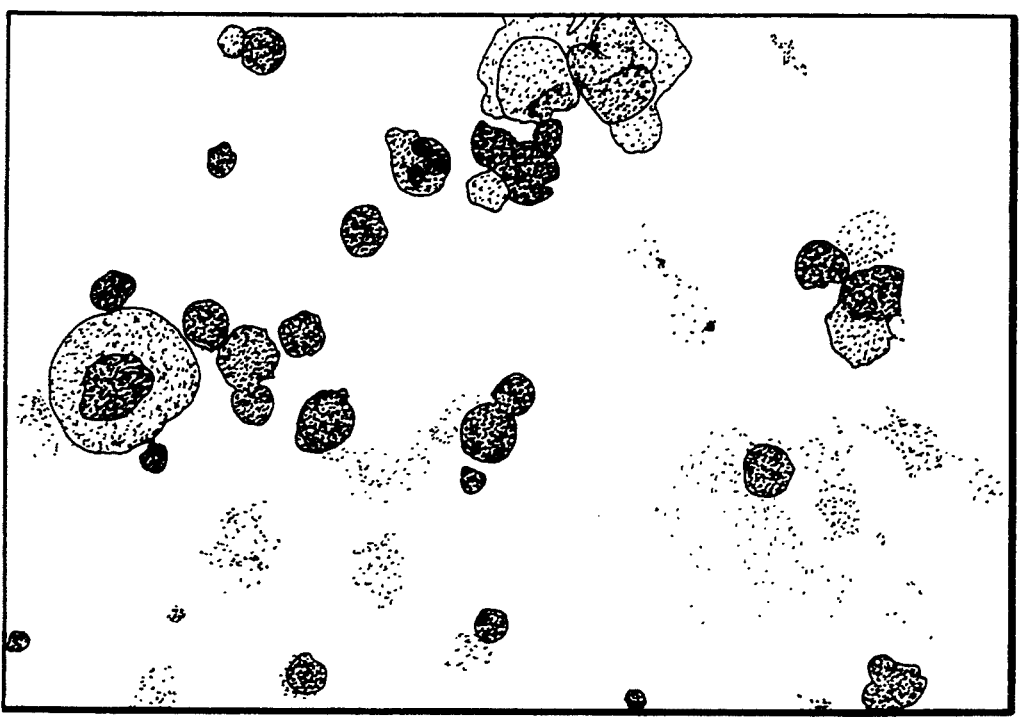
FIG. 8 is photograph of cells which have been treated for 48 hours with Compound 1.
Figure 9:
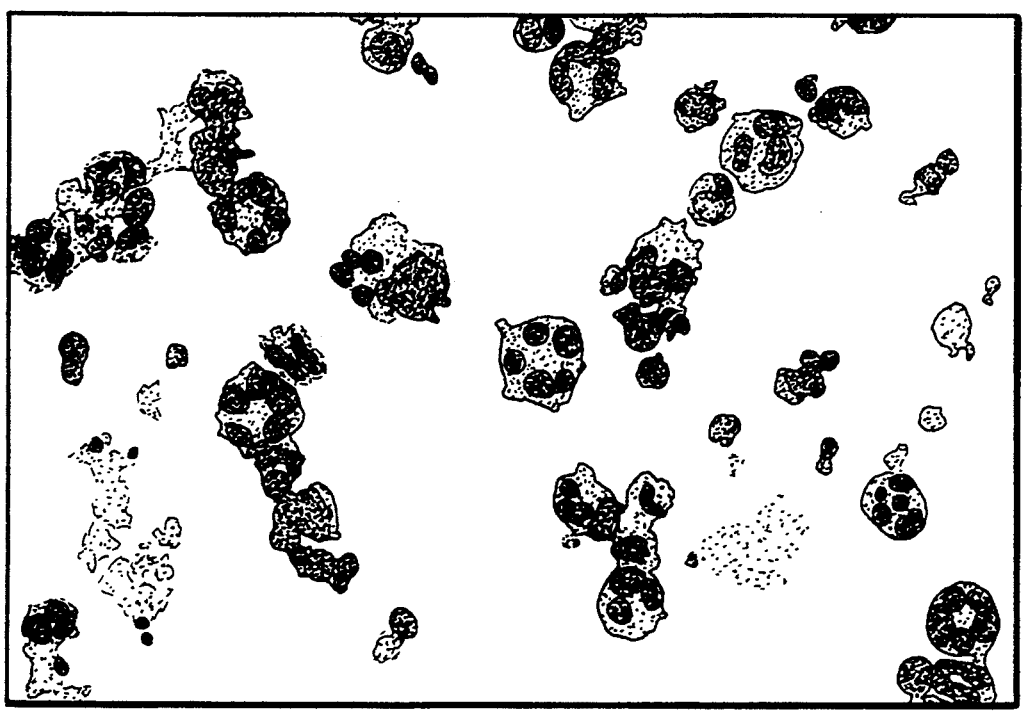
FIG. 9 is photograph of cells which have been treated for 6 days with Compound 1.

FIGS. 5-9 show the results of the above described assays. Specifically, FIG. 5 is a photograph of a DNA "ladder" obtained from cells which had been treated with Compound 1 (AGN 191701) for 48 hours in the above-described assay. FIG. 6 is a photograph, of "control" cells, that is of cells which have been treated with "media" but not with an RXR agonist compound in the just-described assay. FIG. 7 is photograph of cells which have been treated for 4 hours with. Compound 1. FIG. 8 is photograph of cells which have been treated for 48 hours with Compound 1, and FIG. 9 is photograph of cells which have been treated for 6 days with Compound 1. Similar results are obtained when the treatment is with the "pan-agonist" Compound 3 (AGN 191659) in accordance with the invention.

As it can be seen in the photographs, treatment with the RXR agonists induces apoptotic cell death in highly significant number of cells. The use of a compound such as Compound 3 in the method of treatment of the present invention is somewhat less preferred than the use of an RXR specific agonist (such as Compound 1) because RAR agonist activity is known to be associated with side effects which are avoided with RXR specific drugs.

Formulations and Methods of Treatment

The compounds used in the method of treatment of this invention may be administered systemically or topically, depending on such considerations as the condition to be treated, need for site-specific treatment, quantity of drug to be administered, and similar considerations.

In the treatment of certain malignancies topical administration may be used. Any common topical formulation such as a solution, suspension, gel, ointment, or salve and the like may be employed. Preparation of such topical formulations are well described in the art of pharmaceutical formulations as exemplified, for example, by *Remington's Pharmaceutical Science*, Edition 17, Mack Publishing Company, Easton, Pa. For topical application, these compounds could also be administered as a powder or spray, particularly in aerosol form.

In most applications of the novel method of treatment of the present invention, the active ingredient RXR agonist compounds are administered in pharmaceutical compositions adapted for systemic administration. As is known, if a drug is to be a administered systemically, it may be confected as a powder, pill, tablet or the like, or as a syrup or elixir for oral administration. For intravenous, intraperitoneal or intra-lesional administration, the compound will be prepared as a solution or suspension capable of being administered by injection. In certain cases, it may be useful to formulate these compounds in suppository form or as an extended release formulation for deposit under the skin or intermuscular injection.

A therapeutic concentration will be that concentration which effects reduction of the particular condition, or retards its expansion. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of malignancies in accordance with the present invention a formulation containing between 0.001 and 5 percent by weight, preferably about 0.01 to 1%, will usually constitute a therapeutically effective concentration. When administered systemically, an amount between 0.01 and 100 mg per kg body weight per day, but preferably about 0.1 to 10 mg/kg, will effect a therapeutic result in most instances.

General Embodiments

Definitions

The ensuing description provides examples of the RXR agonist compounds which are used in the novel method of treatment of malignancies, in accordance with the present invention.

In the chemical description of the examplary compounds provided here all chemical terms have the meaning normally attributed to them by those skilled in organic chemistry. Thus, the term alkyl refers to and covers any and all groups which are known as normal alkyl, branch-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cyclo-alkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. Preferred esters of the exemplary carboxylic acids within the scope of the present invention are formed with saturated aliphatic alcohols of ten or fewer carbon atoms or the cyclic or saturated aliphatic cyclic alcohols of 5 to 10 carbon atoms, and particularly preferred esters are formed with aliphatic alcohols having 1–10 carbons. Where the ester is derived from compounds within the scope of the present invention which are primary alcohols (B in Formulas 1 is $-CH_2OH$) this term covers compounds of the formula $-CH_2OOCR_{11}$ where $R_{11}$ is any substituted or unsubstituted aliphatic, aromatic or aliphatic-aromatic group, preferably with 1–6 carbons in the aliphatic portions. Particularly preferred aliphatic esters are those derived from lower alkyl acids or alcohols. Also preferred are the phenyl or lower alkylphenyl esters.

Amide has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formulas $-CH(OR_{12})_2$, $-CHOR_{13}O$, $-CR_7(OR_{12})_2$, and $-CR_7OR_{13}O$, where $R_7$ is an alkyl, cycloalkyl or alkenyl group containing 1 to 5 carbons, $R_{12}$ is lower alkyl, and $R_{13}$ is divalent alkyl radical of 2-5 carbons.

A pharmaceutically acceptable salt may be prepared for any compound used in the method of treatment of this invention, if the compound has a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The exemplary compounds utilized in accordance with the method of treatment of the present invention, contain a double bond and therefore have trans and cis (E and Z) isomers. In addition, some of the compounds used in the method of treatment of the present invention may contain one or more chiral centers and therefore exist in enantiomeric and diastereomeric forms. Unless, it is specifically indicated otherwise by chemical nomenclature or structure, the scope of the present invention is intended to cover all such isomers per se, as well as mixtures of cis and trans isomers, mixtures of diastereomers and racemic mixtures of enantiomers (optical isomers) as well. In the structural formulas trans (E) configuration of substituents about a double bond is indicated by bonds pointing in opposite directions about a double bond, whereas cis (Z) configuration of substituents about a double bond is indicated by bonds pointing in the same direction about a double bond.

The general structures of the exemplary RXR agonist compounds which are used in the the pharmaceutical compositions and methods of treatment of the present invention are shown by the general Formula 1 below.

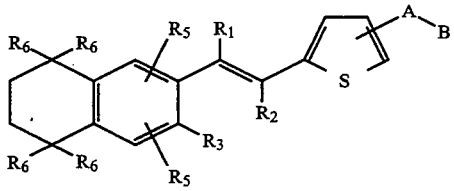

Formula 1

The symbols are defined as follows:
$R_1$ is lower alkyl, Cl, Br, or I;
$R_2$ is H, lower alkyl, Cl, Br, or I;
$R_3$ is lower alkyl, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$, or $NR_{11}$—$COR_{11}$;
the $R_5$ groups independently are H, lower alkyl, Cl, Br, I, lower alkoxy or lower thioalkoxy of 1 to 6 carbons;
the $R_6$ groups independently are H or lower alkyl;

A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2–5 carbons.

Preferred compounds used in the pharmaceuticals compositions and methods of treatment of the present invention are those, where $R_1$ represents lower alkyl, still more preferably methyl. $R_2$ is preferably H or lower alkyl, more preferably H. $R_3$ is preferably lower alkyl, more preferably methyl. $R_5$ preferably is H or lower alkyl, more preferably H. $R_6$ is preferably lower alkyl, more preferably methyl.

With respect to the group —A—B—, compounds are preferred for use in the present invention where —A—B— is a $(CH_2)_n$—$COOR_8$ group, or a $(CH_2)_n$—$CONR_9R_{10}$ group ($R_8$, $R_9$ and $R_{10}$ defined as above), and more preferably where n is zero, and where the B group is $COOR_8$. Most preferably, B is COOH.

Two specific examples of preferred compounds in the method of treatment of the present invention have been shown above by their respective structural formulas, designated as Compound 1 (AGN 191701) and Compound 3 (AGN 191659).

Synthetic Procedures for Obtaining the Compounds in Accordance with the Invention The compounds set forth above as general and specific examples for: use in the pharmaceutical compositions and methods of treatment of the present invention, can be made by a number of different synthetic chemical pathways. To illustrate the invention the following synthetic schemes are provided. The synthetic chemist will readily appreciate that the conditions set out here are specific embodiments which can be generalized within the skill of the practicing synthetic organic chemist.

Reaction Scheme 1

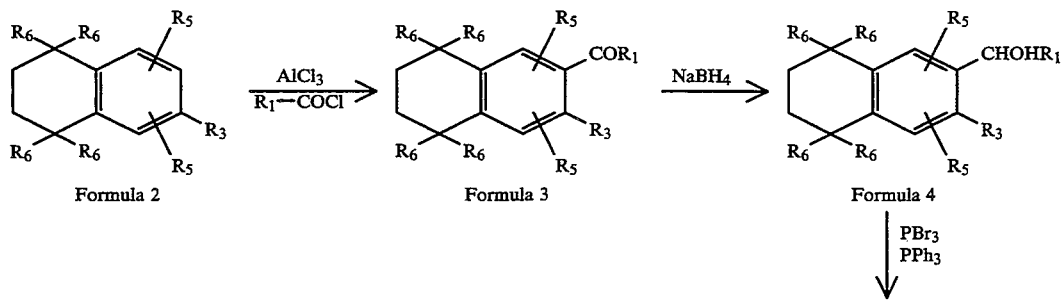

Formula 2   Formula 3   Formula 4

-continued
Reaction Scheme 1

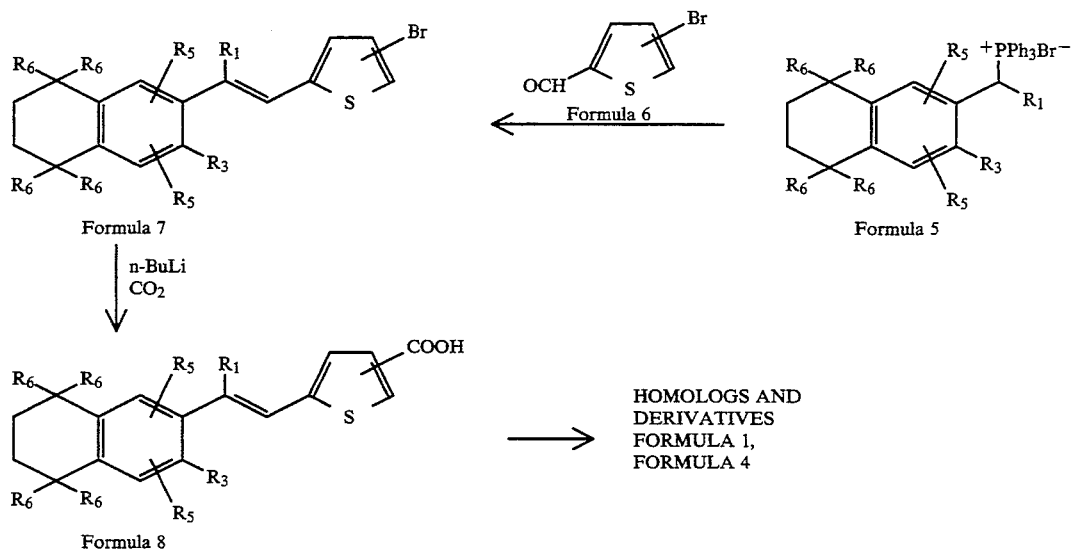

Formula 7

Formula 6

Formula 5

Formula 8

HOMOLOGS AND
DERIVATIVES
FORMULA 1,
FORMULA 4

Reaction Scheme 1 illustrates a synthetic process for obtaining compounds of Formula 1. In accordance with this synthetic scheme, a 5,6,7,8-tetrahydronaphthyl compound of Formula 2 which has the desired $R_3$, $R_5$, and $R_6$ substituents (as these are defined in connection with Formula 1) is reacted under Friedel Crafts-like conditions with a reagent such as $R_1COCl$ ($R_1$ is defined as in connection with Formula 1) to introduce the $R_1$—CO— ketone function into the 2-position of the tetrahydro- naphthalene nucleus. When $R_1$ is methyl, then the reagent in the Friedel Crafts type reaction is typically acetyl chloride. The resulting ketone of Formula 3 is then reduced (for example with sodium borohydride) to the corresponding alcohol of Formula 4. The alcohol of Formula 4 is converted to the corresponding phosphonium salt (for example triphenyl phosphonium bromide) by treatment with the appropriate reagents, such as phosphorous tribromide and triphenylphosphine. The phosphonium salt of Formula 5 is a Wittig reagent, which is reacted with a bromo thiophene aldehyde of Formula 6, under Wittig conditions (base such as n-butyl lithium) to provide compounds of Formula 7. The bromo group of the thiophene moiety of the compound of Formula 7 is converted into a carboxyl group by reaction with n-butyl lithium and capture of carbon dioxide, to yield the carboxylic acid compounds of Formula 8, which can be further converted into further homologs and derivatives, as described herein. The synthetic sequence of Reaction Scheme 1 is the preferred synthetic route for the preparation of Compound 1 (AGN 191701) and Compound 3 (AGN 191659) in accordance with the invention.

An alternative synthetic route leading to compounds of Formula 1 is described with reference to Reaction Scheme 2.

Reaction Scheme 2

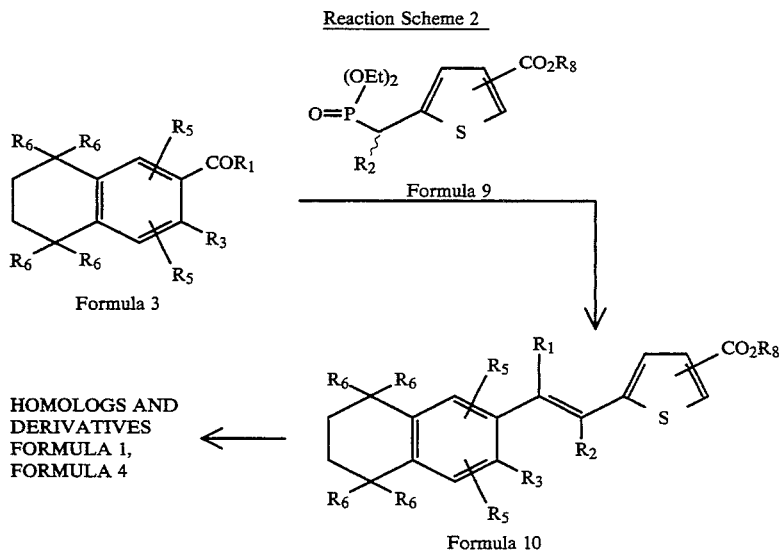

Formula 3

Formula 9

HOMOLOGS AND
DERIVATIVES
FORMULA 1,
FORMULA 4

Formula 10

In accordance with Reaction Scheme 2, the ketone compound of Formula 3 is subjected to a Wittig-Horner type reaction with a phosphonate reagent of Formula 9. The phosphonate reagent of Formula 9 carries an ester ($COOR_8$) substituent, but it should be understood that an analogous phosphonate reagent can, generally speaking, carry the A—B functionality, as such functionality is defined in connection with Formula 1. The Wittig Horner type reaction is typically conducted in the presence of strong base, such as $NaCH_2SOCH_3$ (dimsyl sodium) in a solvent like tetrahydrofuran (THF). The synthetic procedure of Reaction Scheme 2 is preferred, with appropriate selection of the aromatic reagent of the type represented by Formula 9, as the synthetic route for obtaining Compound 2 (AGN 191440) which is the reference compound used in the RXR receptor activity assay.

The compounds of Formula 8 and of Formula 10 may be subjected to further transformations, particularly as far as synthetic transformation of the $COOR_8$ group is concerned. As far as the preparation of compounds analogous to the compounds of Formula 8 and of Formula 10, but differring therefrom in the functionality of the A—B group is concerned, (and by extension of the principles to any and all compounds used in accordance with the invention) the following further well known and published general principles and synthetic methodology are noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before affecting the Wittig reaction, the Wittig Horner reaction, or analogous coupling reactions of Reaction Scheme 1 and Reaction Scheme 2 (where the necessary reagents corresponding to Formula 6 and/or to Formula 9 are not available from a commercial source) the carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

An alternative means for making compounds where A is $(CH_2)_n$ (n is 1-5) is to subject the compounds of Formula 1 where B is an acid or other function, to homologation, using the Arndt-Eistert method referred to above, or other homologation procedures.

Compounds of Formula 1, where A is an alkenyl group having one or more double bonds can be made for example, by having the requisite number of double bonds incorporated into the intermediate which is coupled as a phosphonate with the ketone of Formula 3. Generally speaking, such compounds where A is an unsaturated carbon chain can be .obtained by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of Formula 1 where the A group has a triple (acetylenic) bond can be made by using the corresponding phosphonate intermediate. Such intermediate can be obtained by reactions well known in the art, for example, by reaction of a corresponding aromatic-methyl ketone with strong base, such as lithium diisopropyl amide.

The acids and salts derived from compounds of Formula 1 are readily obtainable from the corresponding esters. Basic saponification with an alkali metal base will provide the acid. For example, an ester may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about $-10$ degrees and $+10$ degrees C. The last mentioned solution is then stirred at the reduced temperature for 1-4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1-4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Referring back again to Reaction Scheme 1 and Reaction Scheme 2, those skilled in the art will readily recognize that further variations of the therein described Wittig and Wittig-Horner reactions are possible to obtain compounds the use of which is within the scope of the present invention. For example, the Wittig reaction shown in Reaction Scheme 1 can be performed with reagents where a tetrahydronaphtalene derivative analogous to Formula 5 bears a keto group, and where a heteroaromatic compound analogous to Formula 6 bears the triphenylphosphonium moiety. The Wittig Horner reaction of Reaction Scheme 2 can be performed with reagents where a tetrahydronaphtalene derivative analogous to Formula 3 bears a dialkylphosphonate moiety and where a heteroaromatic compound analogous to Formula 9 bears a keto or aldehyde function.

SPECIFIC EXAMPLES

Methyl [3,5,5,8,8-pentamethyl(5,6,7,8-tetrahydronaphthalen)-2-yl] Ketone (Compound 10)

To a suspension of 6.71 g (50.3 mmol) of aluminum chloride in methylene: chloride at 0° C. under argon was added a solution of 3.95 g (3.58 mL, 50.3 mmol) of acetyl chloride and 10.2 1 g (41.9 mmol) of 3,5,5,8,8-pentamethyl- 5,6,7,8-tetrahydronaphthalene in methylene chloride. The resulting mixture was allowed to warm to room temperature over a period of 3 hours with stirring. The mixture was recooled to 0° C. and 1N HCl was dropwise added. The mixture was then taken-up in water and extracted three times with methylene chloride. The organic layers were washed with 1N HCl, water, brine, and dried (MgSO$_4$). Solvent was removed in-vacuo and the resulting residue purified using flash chromatography to give the title compound as an ivory solid.

PMR (CDCl$_3$): δ 1.28 (6H, s), 1.30 (6H, s), 1.69 (4H, s), 2.49 (3H, s), 2.57 (3H, s), 7.15 (1H, s), 7.67 (1H, s).

(+)-1-(5,6,7,8-tetrahydro-3,5,5,8,8-pentamethylnaphthalen-2-yl)ethanol (Compound 11)

To a solution of 4.17 g (17.1 mmol) of methyl [3,5,5,8,8-pentamethyl(5,6,7,8-tetrahydronaphthalen-2-yl] ketone (Compound 10) in methanol at 0° C. was portionwise added 0.77 g (20.4 mmol) of sodium borohydride and the resulting suspension stirred at 0° C. for 4 hours. Solvent was removed in-vacuo and the resulting :solid taken-up in water, acidified using 1N HCl, and extracted three times with ether. The ether extracts were washed with water, brine and dried (MgSO$_4$). The solvent was removed in-vacuo and resulting residue purified using flash chromatography (SiO$_2$, 10% ethyl acetate in hexanes) to give a single isomer: the title compound as a white solid.

PMR (CDCl$_3$): δ 1.28 (12H, m), 1.47 (3H, d, J=6.5 Hz), 1.67 (4H, s), 2.49 (3H, s), 5.08 (1H, m), 7.10 (1H, s), 7.45 (1H, s).

[(5,6,7,8-tetrahydro-3,5,5,8,8-pentamethylnaphthalen-2-yl)ethan- 1-yl]triphenylphosphonium Bromide (Compound 12)

To a solution of 3.87 g (15.7 mmol) of (+)-1-(5,6,7,8-tetrahydro-3,5,5,8,8-pentamethylnaphthalen-2-yl)ethanol (Compound 11) in ether and hexanes at 0° C. under argon, was added 42.4 g (14.9 mL, 157 mmol) of phosphorus tribromide and the resulting mixture stirred for 2 hours. Water was then dropwise added over a period of 30 minutes and the layers separated. The aqueous layer was extracted three times with ether. The ether layers were washed with water, brine, and dried (MgSO$_4$). The solvent was removed in-vacuo and the remaining residue taken-up in benzene. Triphenylphosphine was added and the mixture stirred at room temperature for 24 hours. The mixture was then concentrated in-vacuo and the resulting solid recrystallized from acetonitrile and ethyl acetate and hexanes to give the title compound as a white solid.

PMR (CDCl$_3$): δ 0.61 (3H, s), 0.89 (3H, s), 1.27 (6H, s), 1.62 (4H, m), 1.85 (6H, d), 2.04 (3H, dd), 5.19 (2H, m), 6.62 (1H, d), 7.02 (1H, s), 7.43 (6H, m), 7.68 (6H, m), 7.87 (3H, m).

2-[(E)-2-(5,6,7,8-tetrahydro-3,5,5,8,8-pentamethyl-2-naphthalen-2-yl)propen-1-yl]-4-bromothiophene (Compound 13)

To a solution of 0.56 g (0.98 mmol) of 1-(3,5,5,8,8-pentamethyl-5,6,7,8-tetrahydro-naphthalen-2-yl)ethan-1-yltriphenylphosphonium bromide (Compound 12) in 11 mL of tetrahydrofuran at −78° C. under argon was added dropwise 0.41 g (0.61 mL, 0.98 mmol, 1.6M in hexanes) of n-BuLi. The resulting suspension was allowed to warm to room temperature and then a solution of 0.28 g (1.47 mmol) of 4-bromo-2-thiophenecarboxaldehyde in 2 mL of tetrahydrofuran was dropwise added and the resulting mixture stirred for 20 hours at room temperature. The solvent was removed in-vacuo and the resulting solid taken-up in water, acidified using 1N HCl, and extracted three times with ether. The ether extracts were washed with water, brine and dried (MgSO$_4$). The solvent was removed in-vacuo and resulting residue purified using flash chromatography (SiO$_2$, 0.5% ethyl acetate in hexanes) to give the title compound as a white solid.

PMR (CDCl$_3$): δ 1.27 (6H, s), 1.29 (6H, s), 1.68 (4H, s), 2.26 (6H, m), 6.45 (1H, s), 6.75 (1H, s), 6.95 (1H, s), 7.07 (1H, s), 7.11 (1H,, s), 7.17 (1H, s).

2-[(E)-2-5,6,7,8-tetrahydro-3,5,5,8,8-pentamethylnaphthalen-2-yl)propen-1-yl]thiophene-4-carboxylic Acid (Compound 1)

To a solution of 500 mg (1.24 mmol) of 2[-2-(E)-(5,6,7,8-tetrahydro-3,5,5,8,8-pentamethylnaphthalen-2-yl)propen-1-yl]-4-bromothiophene (Compound 13) in 15 mL of tetrahydrofuran stirring under argon at −100° C. was added 0.527 g (0.775 mL, 1.24 mmol, 1.6M in hexanes) of n-BuLi. The reaction was stirred for two minutes and purged with carbon dioxide for 20 minutes. The reaction mixture was then allowed to warm to room temperature, acidified, and extracted using ether. The ether extracts were washed with water, brine and dried (MgSO$_4$). The solvent was removed in-vacuo and the resulting residue taken-up in aqueous 2N sodium hydroxide and washed with ether. The resulting aqueous layer was acidified using 1N HCl and extracted with ether. The ether layer was washed with water and brine, and dried (MgSO$_4$). The solvent was removed in-vacuo and the resulting material purified by flash chromatography (10% ethyl acetate in hexanes) to give the title compound as a white solid.

PMR (d$^6$-DMSO): δ 1.23 (12H, s), 1.62 (4H, s), 2.21 (3H, s), 2.23 (3H, s), 6.56 (1H, s), 7.07 (1H, s), 7.13 (1H, s), 7.45 (2H, s), 8.24 (2H, s).

2-[(E)-(2)-((5,6,7,8-tetrahydro-3,5,5,8,8-pentamethyl-naphthalen-2-yl)-propen-1-yl]-5-bromothiophene (Compound 14)

To a solution of 3.00 g (5.26 mmol) of [(5,6,7,8-tetrahydro-3,5,5,8,8-pentamethylnaphthalen-2-yl)ethan-1-yl]triphenylphosphonium bromide (Compound 12) in 60 mL of tetrahydrofuran at −78° C. under argon was dropwise added 2.24 g (3.29 mL, 5.26 mmol, 1.6M in hexanes) of n-BuLi. The resulting suspension was allowed to warm to room temperature where a solution of 1.01 g (0.63 mL, 5.26 mmol) of 5-bromo-2-thiophenecarboxaldehyde in 10 mL of tetrahydrofuran was dropwise added and the resulting mixture stirred for 20 hours at room temperature and then refluxed for 1 hour. The mixture was acidified using 1N HCL, and extracted three times with ether. The ether extracts were washed with water, brine and dried (MgSO4). The solvent was removed in-vacuo and resulting residue purified using flash chromatography (SiO2, 2% ethyl acetate in hexanes) to give the title compound as a white solid.

PMR (CDCl3): δ 1.28 (12H, s), 1.67 (4H, s), 2.24 (6H, 2×s), 6.45 (1H, s), 6.75 (1H, d, J=3.9 Hz), 6.99 (1H, d, J=3.8 Hz), 7.07 (1H, s), 7.09 (1H, s).

2-[(E)-2-(5,6,7,8-tetrahydro-3,5,5,8,8-pentamethylnaphthalen-2-yl)propen-1-yl]-5-thiophenecarboxylic Acid (Compound 3)

To a solution of 0.230 g (0.57 mmol) of 2-[(E)-2-((5,6,7,8-tetrahydro-3,5,5,8,8-pentamethylnaphthalen-2-yl)propen- 1-yl]-5-bromothiophene (Compound 14) in ether was dropwise added 0.67 mL (1.14 mmol, 1.7M in hexanes) of t-BuLi under argon at −78° C. The resulting mixture was stirred for 1.5 hours, purged with carbon dioxide and allowed to warm to room temperature over a period of 16 hours. The mixture was acidified using 1N HCl and extracted with ether. The ether layer was then washed with water, brine, and dried (MgSO4). Solvent was removed in-vacuo to give a blue solid which was recrystallized using ether in hexanes to give the title compound as a light blue solid.

PMR (d6-DMSO): δ 1.21 (12H, s), 1.60 (4H, s), 2.19 (3H, s), 2.24 (3H, s), 6.45 (1H, s), 6.61 (1H, s), 6.99 (1H, d, J=3.8 Hz), 7.06 (1H, s), 7.12 (1H, s), 7.18 (1H, d, J=3.8 Hz), 7.67 (1H, d, J=3.8 Hz).

Ethyl 2-[(E)-2-(5,6,7,8-tetrahydro-3,5,5,8,8-pentamethylnaphthalen-2-yl)propen-1-yl]-5-thiophenecarboxylate (Compound 15)

A suspension of 0.161 g (0.437 mmol) of 5-[(E)-2-(5,6,7,8-tetrahydro-3,5,5,8,8-pentamethylnaphthalen-2-yl)propen-1-yl]-2-thiophenecarboxylic acid, (Compound 3, 0.03 g, 0.655 mmol) in EtOH, 0.099 g (0.48 mmol) of 1,3-dicyclohexylcarbodiimide, and 5.3 mg (0.044 mmol) of 4-dimethylaminopyridine in 10 mL of methylene chloride was stirred at room temperature for 16 hours. The reaction mixture was filtered and the filtrate washed with water and brine. The organic layers were combined and dried (MgSO4), The solvent was removed in-vacuo and the residue purified using flash chromatography (SiO2, 5% ethyl acetate in hexanes) to give the title compound as a clear oil.

PMR (CDCl3): δ 1.27 (12H, s), 1.39 (3H, t, J=7.2 Hz), 1.68 (4H, s), 2.27 (3H, s), 2.34 (3H, s), 4.37 (2H, q, J=7. Hz), 6.57 (1H, s), 7.00 (1H, d, J=3.8 Hz), 7.09 (1H, s), 7.11 (1H, s), 7.74 (1H, d, J=3.8 HZ).

4-Carboethoxy-benzylbromide (Compound 6 )

To a stirred solution of 16.09 g (78 mmol) of 1,3-dicyclohexylcarbodiimide (Aldrich) in 100 ml methylene chloride was added a suspension of 15.4 g (71 mmol) of 4-carboxybenzylbromide in 100 ml methylene chloride and then 4.9 g (106.5 mmol) of absolute ethanol and 0.81 g (7.1 mmol) of 4-dimethylaminopyridine. A further 50 ml of methylene chloride was added to the reaction mixture and mixture heated at reflux for 2 hours. The mixture was allowed to cool to room temperature and the resultant white precipitate removed by filtration. The filtrate was washed with water, dried MgSO4) and then concentrated in-vacuo to give the title compound as a colorless oil which crystallized on standing. PMR (CDCl3); δ 1.39 (3H, t, J~7.2 Hz), 4.38 (2H, q, J~7.2 Hz), 4.50 (2H, s), 7.45 (2H, d, J~7.7 Hz), 8.03 (2H, d, J~7.7 Hz) .

Ethyl [4-(diethoxyphosphinyl)methyl]benzoate (Compound 17)

A mixture of 11.8 g (48 mmol) of 4-carboethoxybenzylbromide (Compound 16) and 12.0 g (72 mmol) of freshly distilled triethylphosphite was placed in a flask fitted with an argon inlet and a dry-ice cooled trap. A continuous stream of argon was passed over the stirred reaction mixture and mixture heated at 120~° C. for 3 hours at which time no further ethyl bromide was being formed. The residue was purified by vacuum distillation to give the title compound as a colorless oil, BP=70°/0.35 mm). PMR (CDCl3): δ 1.23 (6H, t, J~7.1 Hz), 1.39 (3H, t, J~6.9 Hz), 3.21 (2H, d, J~ 22.1 Hz), 4.02 (4H, m), 4.37 (2H, q, J~7.5 Hz), 7.38 (2H, d, J~7.9 Hz), 8.00 (2H, d, J~7.9 Hz).

Ethyl 4-[(E)-2-(5,6,7,8-tetrahydro-3,5,5,8,8-pentamethylnaphthalen-2-yl)propen-1-yl]benzoate (Compound 18)

A solution of 5.0 g (21.5 mmol) of methyl [3,5,5,8,8-pentamethyl(5,6,7,8-tetrahydro-naphthalen)-2-yl]ketone (Compound 10) and 3.39 g (11.3 mmol) of ethyl [4-(diethoxyphosphinyl)methyl]benzoate, (Compound 17) in 25 mL of tetrahydrofuran was added via cannula into a suspension of 0.52 g (21.5 mmol) of sodium hydride in 25 mL of tetrahydrofuran at 0° C. under argon. The resulting suspension was allowed to warm to room temperature and stirred for 16 hours. The resulting sludge was taken-up in water and 1N HCl and extracted with ether. The ether layers were washed with water, brine, and dried (MgSO4). The solvent was removed in-vacuo and the residue purified using flash chromatography (SiO2, 1% ethyl acetate in hexanes) to give a mixture of isomers which were separated using HPLC (0.5% ethyl acetate in hexanes) to give the title compound as a white solid.

PMR (CDCl3): δ 1.30 (12H, s), 1.38 (3H, t, J=7.0 Hz), 1.69 (4H, s), 2.21 (3H, s), 2.30 (3H, s), 4.39 (2H, q, J=7.1 Hz), 6.42 (1H, s), 7.12 (2H, overl. s), 7.43 (2H, d, J=8.3 Hz), 8.05 (2H, d, J=8.3 Hz).

4-(E)-2-(5,6,7,8-tetrahydro-3,5,5,8,8,-pentamethylnaphthalen-2-yl)propen-1-yl]benzoic Acid (Compound 2)

A solution of potassium hydroxide in ethanol was added to 95 mg (0.25 mmol) of ethyl 4-[(E)-2-(5,6,7,8-tetrahydro-3,5,5,8,8-pentamethylnapth)-2-yl )propen-1-yl]benzoate (Compound 18) and the resulting mixture stirred at room temperature. Solvent was removed in-vacuo and the resulting solid taken-up in water, acidified using 1N HCl, and extracted three times with ether. The ether extracts were washed with water, brine and dried (MgSO$_4$). The solvent was removed in-vacuo to give the title compound as an orange solid.

PMR (d$^6$-DMSO): δ 1.23 (12H, s), 1.62 (4H, s), 2.15 (3H, s), 2.23 (3H, s), 6.37 (1H, s), 7.08 (1H, s), 7.13 (1H, s), 7.51 (2H, d, J=8.3 Hz), 7.94 (2H, d, J=8.3 Hz).

What is claimed is:

1. A process for administering to a host mammal, including a human being, suffering from a tumor, a pharmaceutical composition containing an effective dose of an active compound which has retinoid like activity and is an agonist of RXR retinoid receptors, for the purpose of inducing apoptotic death of the cells of the tumor, and thereby treat the tumor.

2. The process of claim 1 wherein the active compound is a selective agonist of the RXR retinoid receptors in preference over RAR retinoid receptors.

3. The process of claim 1 wherein the active compound is a specific agonist of the RXR retinoid receptors when compared to RAR retinoid receptors.

4. The process of claim 1 wherein approximately 0.01 to 100 mg/kg body weight of the active compound is administered to the mammal per day.

5. The process of claim 4 wherein approximately 0.1 to 10 mg/kg body weight of the active compound is administered systemically to the host mammal per day.

6. The process of claim 1 wherein the active compound has the formula

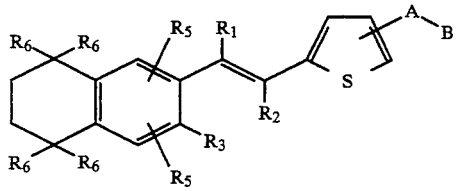

$R_1$ is lower alkyl, Cl, Br, or I;
$R_2$ is H, lower alkyl, Cl, Br, or I;
$R_3$ is lower alkyl, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$, or $NR_{11}$—$COR_{11}$;
the $R_5$ groups independently are H, lower alkyl, Cl, Br, I, lower alkoxy or lower thioalkoxy of 1 to 6 carbons;
the $R_6$ groups independently are H or lower alkyl;
A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds, and
B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of i to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divelent alkyl radical of 2–5 carbons.

7. The process of claim 6 wherein in the formula of the active compound $R_1$, $R_3$ and $R_6$ are methyl, $R_2$ and $R_5$ are hydrogen, and the group —A—B represents $COOR_8$.

8. The process of claim 7 wherein $R_8$ is hydrogen.

9. The process of claim 8 where the $COOR_8$ group is in the 4 position of the thiophene ring.

10. The process of claim 8 where the $COOR_8$ group is in the 5 position of the thiophene ring.

11. A process for administering to a host mammal, including a human being, suffering from a tumor, for the purpose of inducing apoptotic death of the cells of the tumor and thereby to treat the tumor, a pharmaceutical composition containing an effective dose of an active compound having retinoid-like biological activity, which compound has the biological property that the compound is an agonist of RXR retinoid receptors as demonstrated in an assay wherein binding of the compound to RXR receptors is compared to the binding of 4-(E)-2-(5,6,7,8-tetrahydro-3,5,5,8,8-pentamethylnaphthalen-2-yl)propen-1-yl]benzoic acid to the RXR receptors, and in which assay both the active compound and 4-(E)-2-(5,6,7,8-tetrahydro-3,5,5,8,8-pentamethylnaphthalen-2-yl)propen-1-yl]benzoic acid act as agonists of said RXR receptors.

12. The process of claim 11 wherein approximately 0.01 to 100 mg/kg body weight of the active compound is administered systemically to the host mammal per day.

13. The process of claim 12 wherein approximately 0.1 to 10 mg/kg body weight of the active compound is administered systemically to the host mammal per day.

14. The process of claim 12 wherein the active compound has the further biological property that in an assay wherein binding of the compound to RAR receptors is compared to the binding of trans retinoic acid, the compound does not act as a significant agonist of the RAR receptors.

15. A pharmaceutical composition suitable for inducing apoptotic death of tumor cells in a mammal suffering from a tumor, the pharmaceutical composition including a pharmaceutically acceptable excipient and an active compound which has the biological property that the compound is an agonist of RXR retinoid receptors.

16. The pharmaceutical composition of claim 15 wherein the concentration of the active compound is between approximately 0.001 to 5 percent by weight.

17. The pharmaceutical composition of claim 15 wherein the active compound is a specific agonist of RXR retinoid receptors when compared to the activity of said compound on RAR retinoid receptors.

18. The pharmaceutical composition of claim 15 wherein the active compound has the formula

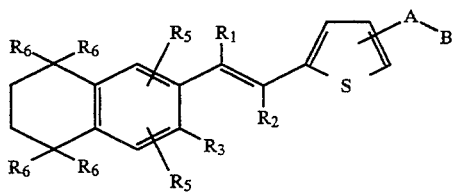

$R_1$ is lower alkyl, Cl, Br, or I;
$R_2$ is H, lower alkyl, Cl, Br, or I;
$R_3$ is lower alkyl, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$, or $NR_{11}$—$COR_{11}$;

the $R_5$ groups independently are H, lower alkyl, Cl, Br, I, lower alkoxy or lower thioalkoxy of 1 to 6 carbons;

the $R_6$ groups independently are H or lower alkyl;

A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2–5 carbons.

19. The pharmaceutical composition of claim 18 wherein in the formula of the active compound $R_1$, $R_3$ and $R_6$ are methyl, $R_2$ and $R_5$ are hydrogen, and the group —A—B represents $COOR_8$.

20. The pharmaceutical composition of claim 19 wherein $R_8$ is hydrogen.

21. The pharmaceutical composition of claim 20 where the $COOR_8$ group is in the 4 position of the thiophene ring.

22. The pharmaceutical composition of claim 20 where the $COOR_8$ group is in the 5 position of the thiophene ring.

* * * * *

UNITED STATES PATENT AND TRADEMARK OFFICE
CERTIFICATE OF CORRECTION

PATENT NO. : 5,399,586

DATED : March 21, 1995

INVENTOR(S) : Davies et al.

It is certified that error appears in the above-identified patent and that said Letters Patent is hereby corrected as shown below:

Column 2, line 17, before "Acid" please delete".";

Column 2, line 19, "subtype:s" should be --subtypes--;

Column 11, line 39, after "mM" please delete ",";

Column 12, line 61, after "photogrph" please delete ",";

Column 12, line 65, after "with" please delete".";

Column 16, ine43, after "for" please delete ":";

Column 21, ine 24, "10.2 1" should be --10.21--;

Column 21, line 47, before "solid" please delete":'";

Column 21, line 38, "(+)" should be --'(+)--;

Column 24, line 1, "Compound 6" should be --Compound 16--;

Column 24, line 13, before "$MgSO_4$" please insert --(--;

Column 24, line 31, "70°" should be --170°--;

Column 25, line 61, "i to 10" should be --1 to 10--;

UNITED STATES PATENT AND TRADEMARK OFFICE
CERTIFICATE OF CORRECTION

PATENT NO. : 5,399,586
DATED : March 21, 1995
INVENTOR(S) : Davies et al.

It is certified that error appears in the above-identified patent and that said Letters Patent is hereby corrected as shown below:

Column 2, line 43, "comounds" should be --compounds--;

Column 4, line 22, "a a" should be --a--;

Column 4, line 54, "undertod" should be --understood--;

Column 14, line 27, "Formulas" should be --Formula--;

Column 16, line 20, "pharmaceuticals" should be --pharmaceutical--.

Column 26, line 18

Signed and Sealed this

Thirtieth Day of January, 1996

Attest:

BRUCE LEHMAN

Attesting Officer

Commissioner of Patents and Trademarks